United States Patent
Dama et al.

(10) Patent No.: US 9,902,027 B2
(45) Date of Patent: Feb. 27, 2018

(54) INSTRUMENT CHANGING ASSEMBLY AND METHODS

(71) Applicant: Hysitron, Inc., Eden Prairie, MN (US)

(72) Inventors: Rajiv Dama, Chanhassen, MN (US); Svetlana Zigelman, Minnetonka, MN (US)

(73) Assignee: Hysitron, Inc., Eden Prairie, MN (US)

( * ) Notice: Subject to any disclaimer, the term of this patent is extended or adjusted under 35 U.S.C. 154(b) by 104 days.

(21) Appl. No.: 14/908,809

(22) PCT Filed: Aug. 1, 2014

(86) PCT No.: PCT/US2014/049379
§ 371 (c)(1),
(2) Date: Jan. 29, 2016

(87) PCT Pub. No.: WO2015/017765
PCT Pub. Date: Feb. 5, 2015

(65) Prior Publication Data
US 2016/0169718 A1    Jun. 16, 2016

Related U.S. Application Data

(60) Provisional application No. 61/861,306, filed on Aug. 1, 2013.

(51) Int. Cl.
*G01D 21/00* (2006.01)
*B23P 19/04* (2006.01)
(Continued)

(52) U.S. Cl.
CPC .............. *B23P 19/04* (2013.01); *G01N 3/42* (2013.01); *G01Q 60/366* (2013.01); *G01Q 70/02* (2013.01);
(Continued)

(58) Field of Classification Search
CPC .... G01D 5/12; G01L 1/18; G01L 3/02; G01R 1/0408; G01R 1/44; G01R 31/00;
(Continued)

(56) References Cited

U.S. PATENT DOCUMENTS 5,327,657 A    7/1994  Hajdukiewicz et al.
6,352,861 B1 *  3/2002  Copeland .............. B01F 5/0057
                                                    141/130
(Continued)

FOREIGN PATENT DOCUMENTS

KR    1020160030335 A    3/2016
KR        101712028      2/2017
(Continued)

OTHER PUBLICATIONS

"International Application Serial No. PCT/US2014/049379, International Search Report dated Nov. 13, 2014", 3 pgs.
(Continued)

*Primary Examiner* — Harshad R Patel
*Assistant Examiner* — Brandi Hopkins
(74) *Attorney, Agent, or Firm* — Schwegman Lundberg & Woessner, P.A.

(57) ABSTRACT

An instrument changing assembly includes a magazine having one or more probe assembly stations. The assembly further includes at least one probe change tool including a receptacle socket. One or more probe assemblies are retained within the one or more probe assembly stations. The one or more probe assemblies each include a probe receptacle including a probe retention recess and a common socket fitting configured for complementary fitting with a common receptacle socket. The probe change tool is configured to install or extract the respective probes from a mechanical testing instrument according to the complementary fit between the common socket fitting and the common
(Continued)

receptacle socket of the probe assemblies. Alternatively, the instrument changing assembly includes an instrument array housing including a plurality of instruments. Each of the one or more instruments (probe and transducer combination) are deployed relative to the instrument array housing with an instrument deployment actuator.

32 Claims, 11 Drawing Sheets

(51) Int. Cl.
<br>    *G01N 3/42*         (2006.01)
<br>    *G01Q 60/36*       (2010.01)
<br>    *G01Q 70/02*       (2010.01)
<br>    *B23P 19/10*        (2006.01)
<br>    *G01D 18/00*       (2006.01)
<br>    *G01N 19/04*       (2006.01)

(52) U.S. Cl.
<br>    CPC .............. *B23P 19/10* (2013.01); *G01D 18/00* (2013.01); *G01N 19/04* (2013.01); *G01N 2203/0078* (2013.01); *G01N 2203/0202* (2013.01); *G01N 2203/0206* (2013.01); *G01N 2203/0286* (2013.01)

(58) Field of Classification Search
<br>    CPC ................... B81C 99/005; G01N 3/42; G01N 2203/0051; G01N 2203/0617; G01N 19/00; G01N 3/40; G01N 2203/0286; G01N 2203/0082; G01N 2203/0208; G01N 2203/0682; G01N 2203/0092; G01N 2203/021; G01Q 60/366; Y10S 977/956; G01B 7/34
<br>    USPC ..... 73/862.625, 81, 105, 866.5, 852, 56, 82, 73/83, 800
<br>    See application file for complete search history.

(56) References Cited

U.S. PATENT DOCUMENTS

| | | |
|---|---|---|
| 6,538,254 B1 | 3/2003 | Tomimatsu et al. |
| 8,196,458 B2 | 6/2012 | Bonilla et al. |
| 2012/0119770 A1* | 5/2012 | Baekbo .............. G01R 1/06733 324/750.22 |
| 2013/0319127 A1* | 12/2013 | Vodnick ............... G01B 21/047 73/788 |

FOREIGN PATENT DOCUMENTS

| | | |
|---|---|---|
| SG | 11201600737 T | 2/2017 |
| WO | WO-2011121348 A1 | 10/2011 |
| WO | WO-2012109577 A2 | 8/2012 |
| WO | WO-2015017765 A2 | 2/2015 |
| WO | WO-2015017765 A3 | 2/2015 |

OTHER PUBLICATIONS

"International Application Serial No. PCT/US2014/049379, Written Opinion dated Nov. 13, 2014", 11 pgs.
<br>"European Application Serial No. 14831561.7, Extended European Search Report dated Jan. 18, 2017", 9 pgs.
<br>"International Application Serial No. PCT/US2014/049379, International Preliminary Report on Patentability dated Feb. 11, 2016", 8 PGS.
<br>"Korean Application Serial No. 10-2016-7005442, Office Action dated Jul. 14, 2016", 3 pgs.
<br>"Korean Application Serial No. 10-2016-7005442, Response filed Sep. 8, 2016 to Office Action dated Jul. 14, 2016", W/ English Translation of Claims, 19 pgs.
<br>"Singapore Application Serial No. 11201600737T, Written Opinion dated Apr. 11, 2016", 5 pgs.

* cited by examiner

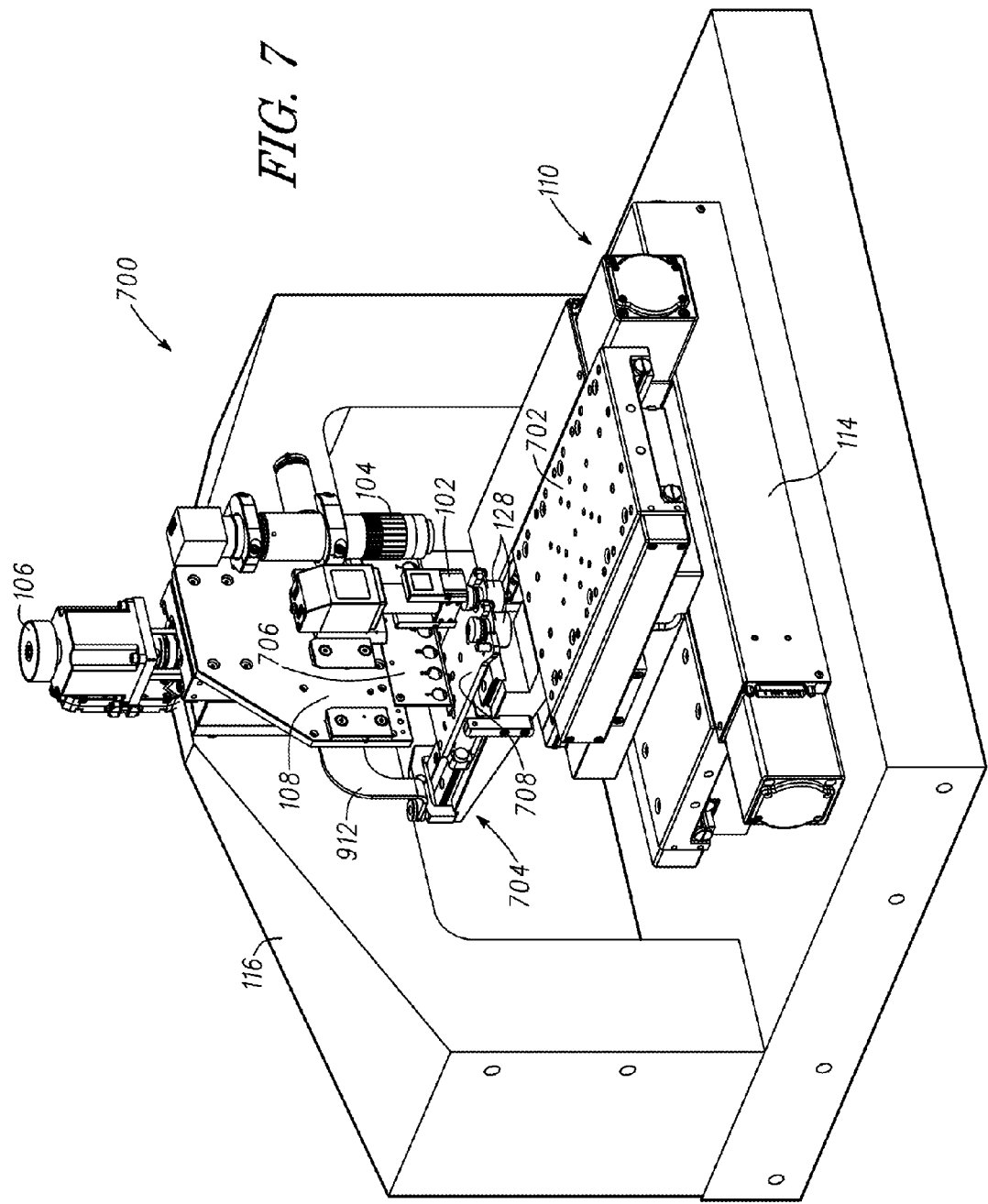

INSTRUMENT CHANGING ASSEMBLY AND METHODS

CLAIM OF PRIORITY

This application is a U.S. National Stage Application under 35 U.S.C. 371 from International Application No. PCT/US2014/049379, filed Aug. 1, 2014 published as WO 2015/017765 A2 on Feb. 5, 2015 and republished on Oct. 15, 2015 as WO 2015/017765 A3, which application claims the benefit of priority to U.S. Provisional Application Ser. No. 61/861,306, filed on Aug. 1, 2013, which is hereby incorporated by reference herein in its entirety.

TECHNICAL FIELD

This document pertains generally, but not by way of limitation, to one or more of automated selection, installation and use of instruments.

BACKGROUND

Mechanical testing at scales of microns or less (e.g., from scales of microns to nanometers) is a technique used to derive mechanical properties at these scales. This is achieved by mechanically testing (e.g., scratching, indenting, tensioning or the like) a sample material with a probe and determining or measuring the forces applied (ranging from a few nano-Newtons to several Newtons) as well as measuring the depth of the corresponding indentation or other mechanical deformation to the sample material.

Probes (e.g., tips for a mechanical testing instrument that indents, scratches material or the like) used for mechanical testing at scales of microns or less come in a variety of geometries, shapes, and materials. Similarly, transducers used with the probes are configured differently to provide a variety of testing functionality (e.g., high load or low load transducers). Certain material properties are better characterized using a particular type of probe (and optionally differing transducers). Users of nano-indenters (and other testing instruments usable at these scales) use different instruments (e.g., one or more of probes or transducers) on the same material to characterize the properties of the material accurately. In some examples, to measure the properties of a material with differing probes users change the probes on the indenter transducers manually between each measurement. Manual changing of the probes significantly increases the overall measurement time (e.g., by way of removal of the previous probe and installation of a new probe, recalibration, test indentations and the like). Additionally, in other examples the manual changing of probes introduces error in mechanical testing as the exchange of probes disturbs a potentially controlled environment, for instance with the exposure of unconditioned (heated or cooled) air, manual manipulation of the instrument and transducer, or the like. Furthermore, changing the probes can be labor intensive and often frustrating, as the small probe sizes (and sensitive instruments) are difficult to hold and mechanically manipulate.

Further, probe geometry (e.g., shape and size) is important for the accuracy of measurements with mechanical testing at scales of microns or less. Probe geometry degrades with usage. In other words, each mechanical testing operation wears the probe and accordingly changes its shape and size. In some examples, software algorithms for nano-indenters (and other mechanical testing instruments at scales of microns or less) implement techniques to detect probe degradation. However, once a worn probe is detected manual changing of the probe may introduce the issues described above. Such an arrangement may be problematic for users running mechanical testing measurements at scales of microns or less over a desired extended timeframe (e.g., on an ongoing or automated basis). Probe degradation may limit the overall timeframe of such extended (repeated) measurements.

Accordingly, the changing of probes and probe degradation may limit the ability to conduct automated measurements with mechanical testing instruments at scales of microns or less.

OVERVIEW

We have developed an instrument changing assembly that changes one or more of the probe or the transducer/probe combination automatically. An instrument assembly, as described herein refers to an overall instrument device including, but not limited to, one or more of a base, stage for samples, and one or more instruments including an instrument mechanism such as a transducer and associated probe. An instrument, as described herein, refers to one or more of a probe, an instrument mechanism such as a transducer usable with the probe, a combination of the probe and instrument mechanism or the like. Methods are described herein that automate the retrieval, installation and extraction of probes used in mechanical testing at scales of microns or less. In a similar manner, another example of the assembly described herein allows for the exchange of a plurality of instruments (e.g., transducers with associated probes) to facilitate automated exchange of instruments. As used herein, "automation" and all versions of the word are intended to encompass, but not be limited to, robotic movement and operations. The systems provided herein automate the manipulation and handling of instruments including, but not limited to, probes and probe receptacles, transducers, combinations of probes and transducers or the like and thereby minimizes manual (and time consuming) interaction with the probes, sensitive transducers of mechanical testing instruments and the like.

The probe change assembly (an example of an instrument changing assembly) consists of a magazine to store probes, a mechanism to retrieve a probe from a transducer of the mechanical testing instrument (e.g., a nano-indenter; three dimensional transducer configured for indenting, scratching or the like; or the like) and store it in or on the magazine. Additionally, the assembly includes a mechanism for retrieval of a probe from the magazine and insertion of the probe into the transducer assembly of the mechanical testing instrument. The assembly, for instance one or more probe change tools applies appropriate torques for inserting and extracting the probes to and from the transducers. For instance, a probe change tool provides an extraction torque for extraction of a probe from the transducer greater than an insertion torque (less than the extraction torque) for insertion of a probe. Optionally, a torque limiting clutch (e.g., with an adjustable slipping interface) is used to govern the insertion torque.

Furthermore, the assembly includes a one or more probe assemblies each including a probe receptacle and a probe coupled with the probe receptacle. The probe receptacles hold the probes in the magazine and serve as an interface between the at least one probe change tool and the probe. During movement (e.g., between the magazine and the mechanical testing instrument transducer) the probe receptacle carries the probe. Additionally, each of the probe receptacles provides a consistent common interface with a socket of the probe change tool. In one example, the common interface includes a socket fitting that is coupled with a receptacle socket of the probe change tool. The socket fitting and the receptacle socket are complementary to ensure consistent coupling and transmission of the extraction and insertion torques to the probe from the probe change tool. Optionally, the complementary fitting is realized without difficult-to-couple interfaces, such as threading. Instead, the complementary fittings are achieved by lowering the probe receptacle and the socket fitting for mating with the receptacle socket of the probe change tool. In still another example, the socket fittings of the probe receptacles align with the receptacle socket of the probe change tool with one or more drive flanges (e.g., magnetic drive flanges, pins or the like) that facilitate the alignment and retention of the probe receptacle (and a probe coupled to the receptacle) on the probe change tool, for instance during movement of the probe assembly and insertion and extraction operations.

The probe side of each of the probe receptacles is provided with a probe retention recess that is sized and shaped for a particular probe configuration. Stated another way, the probe retention recess has a complementary size and shape to a desired probe and thereby provides a snug complementary fit between the probe receptacle and the probe. Accordingly, probe receptacles with differing probe retention recesses allow for installation and extraction of any number of a variety of probes having varied shapes and sizes through the interface of the probe receptacles and the probe change tool (e.g., at the consistently shaped and sized socket fittings of the probe receptacles and receptacle sockets of the probe change tools).

The systems also includes methods (e.g., computer implemented instructions, controller, or the like) that provide control for the above described functionality. The methods control the operation of the mechanical testing instrument (e.g., one or more stages such as x, y and z stages), the magazine, an actuator for an optional telescoping arm, and the one or more probe change tools. The methods allow for a user to select a probe and install it automatically (e.g. robotically) into the transducer, exchange a current probe in the transducer with a different probe, or remove a probe from the transducer and save it in the magazine (replace it in one or more probe assembly stations). Optionally, the methods provide supplemental capabilities including, but not limited to, automatically exchanging a probe in the transducer with a different probe in the magazine (based on user defined or default wear and wear detection settings) once it detects probe degradation. The ability to automatically change probes during an extended measurement scheme (conducting multiple measurements over an extended period of time) provides the user with systems and method to characterize a material sample with multiple probes (optionally having different shapes, sizes, materials or the like). Further, the ability to automatically change probes during an extended measurement scheme facilitates near continuous measurements as probes are readily extracted and replaced and measurements are then continued with minimal pause.

Additionally, in other examples the systems store and retrieve pertinent calibration and other relevant information about each probe from an internal database immediately prior to use of an automatically installed probe in a testing procedure. In another example, the systems automatically calibrate the transducer and property determination functions according to the retrieved calibration information of the probe (as well as other data including wear and probe shape functions updated for wear). In still another example, the systems write the probe information into the measurement data and thereby provides a record of the probe used, its wear and other information of interest for later review.

In yet another example, the systems and methods provided herein also facilitate the calibration of the mechanical testing instrument transducer through two or more calibration probes (e.g., calibration weights). In one example, the two or more calibration probes are retained in respective probe receptacles housed in the magazine. Through installation of each of the probes, corresponding measurement of the transducer response to each of the probes (varying because of their differing weights), and comparison to predicted responses the transducer is calibrated automatically without time consuming and inefficient transducer calibration schemes that require one or more manual interactions with the mechanical testing instrument or time consuming test indentations. Stated another way, because of the automated nature of the systems and methods complex calibration procedures are implemented rapidly and without time consuming training of users and manual interaction with the systems. Additionally, the transducer calibration routines are optionally further enhanced with additional calibration probes (e.g., calibration weights) and further examination of the transducer response.

In yet another example, an example of an instrument changing assembly is provided that includes a plurality of deployable instruments (e.g., in an example transducers, transducer and probe combinations or the like). Each of the instruments includes, in one example, a dedicated transducer and probe. The instruments are operated as described herein to engage a sample and determine one or more characteristics (mechanical, electrical or the like) of the material. In one example, the plurality of instruments are identical and are cycled (e.g., on a translating or rotating housing) as one or more of the instruments (one or both of the probe or transducer) experiences wear or a degradation of performance. Optionally, a degraded instrument of the plurality is recalibrated or replaced (e.g., with a probe change tool described herein or by exchange of a transducer) while one of the other instruments continues to conduct testing operations.

In another example, the plurality of instruments of the instrument changing assembly differ and provide a suite of differing testing capabilities. For instance, one or more of the transducers or probes vary relative to the remainder of transducers or probes. The transducers may vary according to the load applied by each of the transducers (high or low load), axis of transducer movement (x, y, z, pushing or pulling) a combination thereof or the like. Similarly, the probes may vary according to the testing parameters of the respective instrument (e.g., have differing shapes, sizes, materials or the like). In one arrangement of such a system, the plurality of instruments are moved into corresponding positions to test an identified location of a sample material. For instance, the plurality of instruments are indexed to each other according to known spacing. The instruments are each movable into substantially the same location to test the identified location based on the known spacing relative to each other. Conversely, in another example the sample is moved (e.g., by a movable stage) relative to the indexed instruments to allow for testing at substantially the same location with each of the instruments.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 7 is a perspective view of an instrument assembly including another example of an instrument changing assembly configured for changing probes of the instrument assembly.

DETAILED DESCRIPTION

Figure 1:
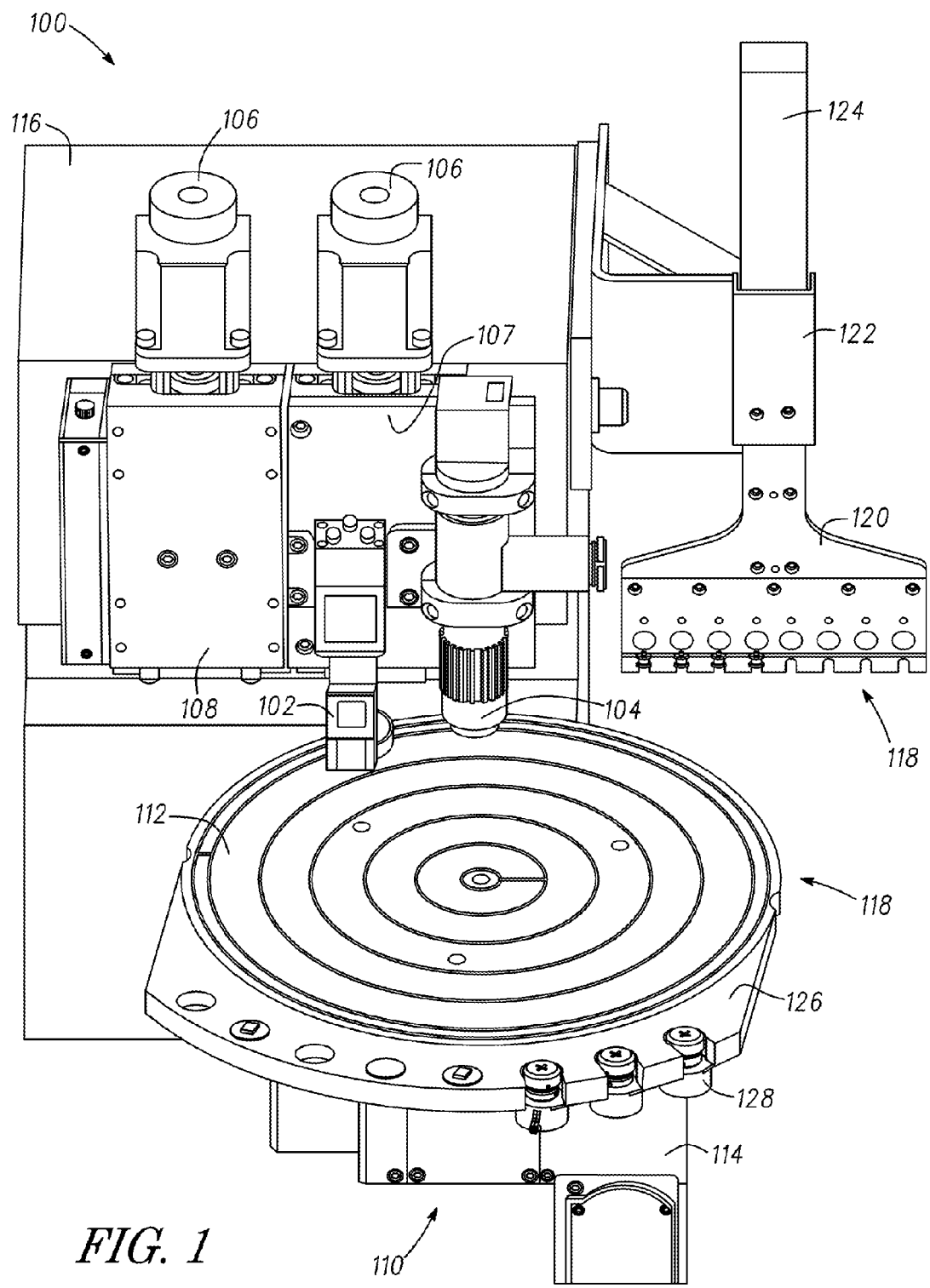
FIG. 1 is a perspective view of one example of an instrument assembly including one example of an instrument changing assembly configured for changing probes of the instrument assembly.

FIG. 1 shows one example of an instrument assembly 100. As shown, the exemplary instrument assembly 100 includes an instrument assembly base 116 (e.g., a granite base or other rigid base resistant to vibration). Extending from the instrument assembly base 116 is at least one testing instrument 102. For instance the testing instrument 102 is movably positioned on the instrument assembly base 116 with an instrument actuator 106 coupled between the base 116 and a primary instrument mount 107. The testing instrument 102 includes an instrument configured to provide one or more of mechanical or electrical characteristic testing of samples. For instance, the testing instrument 102 provides mechanical or electrical characteristic testing of a sample at scales of microns or less. For instance, the testing instrument 102 conducts testing operations including, but not limited to, one or more of indentation, scratching, pushing (compression loading), pulling (tension loading), creep analysis, electrical characteristic testing or the like. Analysis conducted with the testing instrument 102 provides characteristic information about a sample tested including, but not limited to, elastic modulus, hardness, creep characteristics, resistivity or the like.

As further shown in FIG. 1, in one example the testing instrument 102 and an optional optical instrument 104 are mounted on the primary instrument mount 107 and the instrument actuator 106 is configured to move the instruments 102, 104 together. In one example the optical instrument 104 allows for viewing of a sample positioned on the sample stage surface 112 and identification of a testing location on the sample. After identification of the testing location with the optical instrument 104 the testing instrument 102 is moved by way of movement in one or more of the sample stage surface 112 or the instrument actuator 106 to position the testing instrument 102 in alignment with the identified location. As described herein, the testing instrument 102 is lowered or the sample stage surface 112 is raised to position a probe of the testing instrument 102 adjacent to the identified location for testing at the identified location. In one example, the testing instrument 102 described herein is configured to perform one or more testing schemes at the identified location including, but not limited to, indentation, scratching, pulling (tension loading), pushing (compression loading) or the like at the identified testing location. In another example the testing instrument 102 is configured to conduct other tests including for instance electrical characteristic tests at the identified testing location (e.g., the testing instrument 102 and optionally the sample stage surface 112 include electrical contacts to facilitate testing).

As previously described herein the instrument assembly 100 includes one or more testing instruments 102. In the example shown in FIG. 1 a secondary instrument mount 108 is provided. A second instrument actuator 106 is associated with the secondary instrument mount 108. In such an example, a testing instrument similar in at least some regards to the testing instrument 102 is coupled to the secondary instrument mount 108 and is accordingly movable in a similar fashion to the testing instrument 102 positioned on the primary instrument mount 107. In another example the secondary instrument mount 108 includes a testing instrument configured to provide differing testing capabilities relative to the testing instrument 102. For instance a secondary instrument provided on the secondary instrument mount 108 provides one or more differing testing capabilities, for instance a pulling testing scheme (tension loading) relative to a pushing testing scheme (compression loading, indentation, or the like) of the primary instrument 102, high or low load tests for instance with a high load transducer at the secondary instrument mount 108 and a low load transducer at the primary instrument mount for the testing instrument 102 shown in FIG. 1. In some examples, high load transducers are configured to provide actuating forces to a probe of up to 10-15 Newtons. In other examples, low load transducers are configured to provide actuating forces to a probe from milli-Newtons to less than one micro-Newton.

In still another example the secondary instrument provided on the secondary instrument mount 108 is identical to the testing instrument 102. In such an example the testing instruments allow for the selective use of either of the testing instruments 102 as desired. For instance as the testing instrument 102 on the primary instrument mount 107 becomes worn, fails or the like (e.g., a probe or transducer is worn or fails) that testing instrument is cycled out and replaced by the secondary instrument provided on the secondary instrument mount 108 with minimal delay between testing operations. While using the second instrument on the secondary instrument mount 108 a probe changing assembly, such as the probe changing assembly 118 described herein, is used to change out a worn probe from the first instrument and install a replacement probe with the (first) testing instrument 102. Thereafter, the testing instrument 102 is returned to service or held ready until the performance of the (secondary) testing instrument degrades, and accordingly requires replacement of the probe associated with the (secondary) instrument.

As further shown in FIG. 1, a sample stage assembly 110 is provided with the instrument assembly 100. In one example the sample stage assembly 110 is coupled with the instrument assembly base 116. The sample stage assembly 110 is coupled with the instrument assembly base 116 to hold a sample on a sample stage surface 112 substantially static relative to the testing instrument 102. Additionally, the structurally rigid instrument assembly base 116 also holds the testing instrument 102 and the optical instrument 104 static relative to the sample stage surface 112 and a sample positioned thereon.

As shown in FIG. 1, stage actuators 114 are positioned beneath the sample stage surface 112. In one example the stage actuators 114 include one or more actuators configured to provide corresponding movement to the sample stage surface 112 and thereby position varying portions of the sample stage surface 112 (and a sample) relative to the testing instrument 102. For instance, the stage actuators 114 are configured to position one or more identified testing locations of the sample positioned on the sample stage surface 112 beneath or in alignment with the testing instrument 102. In one example, the stage actuators 114 provide one or more of "x," "y," "z" and rotational (θ) movement to the sample stage surface 112 to thereby position substantially any portion of the sample stage surface 112 (including a stage receptacle flange 126 of the probe changing assembly 118 described herein) relative to the testing instrument 102.

In yet another example, the stage actuator 114 includes a limited number of actuators. For instance the stage actuators 114 include an "x" actuator and a rotational (θ) actuator. In such an example a combination of "x" and rotational movement positions substantially any portion of the sample stage surface 112 (as well as the stage receptacle flange 126) in alignment with the testing instrument 102. In such an example the stage actuators 114 through a combination of translational (e.g., along a single axis) and rotational movement are able to minimize the overall footprint of the instrument assembly 100 by accordingly rotating and translating the sample stage surface 112 in a tight footprint relative to the testing instrument 102. Stated another way, instead of using both "x" and "y" translational movements of the stage actuators 114 to position all or many of the locations on the sample stage surface 112 in alignment with the testing instrument 102 stage actuators 114 instead rotate the sample stage surface 112 and thereafter provide limited translational range to the sample stage surface 112 for instance equivalent to one radius of the sample stage surface 112 to accordingly align substantially any location on the sample stage surface 112 with the testing instrument 102.

Referring again to FIG. 1, the instrument assembly 100 is shown including an instrument changing assembly, such as the probe changing assembly 118. As shown the probe changing assembly 118 includes a feature configured to hold a plurality of probes for use by the testing instrument 102. As shown in FIG. 1 this feature is provided by a probe magazine 120 coupled with the instrument assembly base 116. As shown the probe magazine 120 includes a plurality of locations (stations, receptacles, ports, slots or the like) for a corresponding plurality of probes. The probe magazine 120 includes a magazine neck 124 extending upwardly relative to the plurality of probe locations provided near the bottom of the probe magazine 120. The magazine neck 124 is optionally received within a magazine actuator 122 coupled with the instrument assembly base 116. The magazine actuator 122 is configured to provide movement to the probe magazine 120. In one example the magazine actuator 122 lowers and raises the probe magazine 120 to position one or more probes relative to a probe change tool described further herein.

As shown in FIG. 1, the probe magazine 120 is configured to hold a plurality of probe assemblies. For instance as shown in FIG. 1, eight stations are provided on the probe magazine 120. In one example, the probe magazine 120 holds a plurality of probe assemblies having identical probes for use with a testing instrument 102. In another example the probes held by the probe magazine 120 vary. For instance the probes include a variety of differing materials, shapes, sizes, functions (e.g., indenting, scratching, pulling) or the like. Accordingly, with the installation of the varying probes to the testing instrument 102 the capabilities of the testing instrument 102 are varied according to the probe installed. In the example with identical probes stored in the probe magazine 120 the testing instrument 102 may be used in a near continuous manner as the probes are changed in an automated rapid fashion as the probe performance changes or degrades over time. Stated another way, the probe changing assembly 118 allows for the automated extraction of a worn or degraded probe from the testing instrument 102 and corresponding installation of a new probe therein.

In still another example, the probe 120 includes one or more diagnostic probes use to calibrate the testing instrument 102, for instance the transducer of the instrument 102. The diagnostic probes include one or more known test weights. When installed (with the probe changing assembly 118) the known weights are used in one or more diagnostic schemes to measure the mechanical response of the transducer and accordingly calibrate the transducer for the instrument assembly 100.

In yet another example probes provided in the probe magazine 120 include one or more indexed characteristics. For instance the probes provided in the probe magazine 120 include one or more characteristics, such as calibration data, unique to each respective probe. As the probes are loaded into the probe magazine the characteristics are indexed to the probe location on the magazine. For instance, a bar code is read from packaging, from the probe itself, an RFID chip is scanned, catalog information is input or the like to a controller associated with the probe magazine 120 and the instrument assembly 100. Accordingly, corresponding characteristics to each probe, such as calibration values, probe shape, weight, material or the like are indexed to that particular probe location. As the probe is removed from the corresponding probe location (e.g., probe assembly station) and thereafter installed in the testing instrument 102 the controller of the overall instrument assembly 100 automatically configures (calibrates) the testing instrument 102 according to the newly installed probe. In such an example, calibration of the testing instrument 102 for a particular probe type is unnecessary (though it may be performed as to confirm characteristics). Instead, the characteristics of the probe are automatically accessed by the instrument assembly 100 to thereby automatically calibrate the testing instrument 102 according to the unique characteristics of the newly installed probe.

As further shown in FIG. 1, the probe changing assembly 118 includes one or more probe change tools 128. In the example shown the probe changing assembly 118 includes a plurality of probe changing tools 128 installed in a stage receptacle flange 126. The probe change tools 128 are installed within the stage receptacle flange 126 to accordingly use the stage actuators 114 to move the probe change tools 128 between the probe magazine 120 and the testing instrument 102. In another example, the probe change tools 128 are provided on a dedicated arm (as described herein) and are movable relative to the testing instrument 102 the probe magazine 120 (and the sample stage assembly 110).

Figure 2:
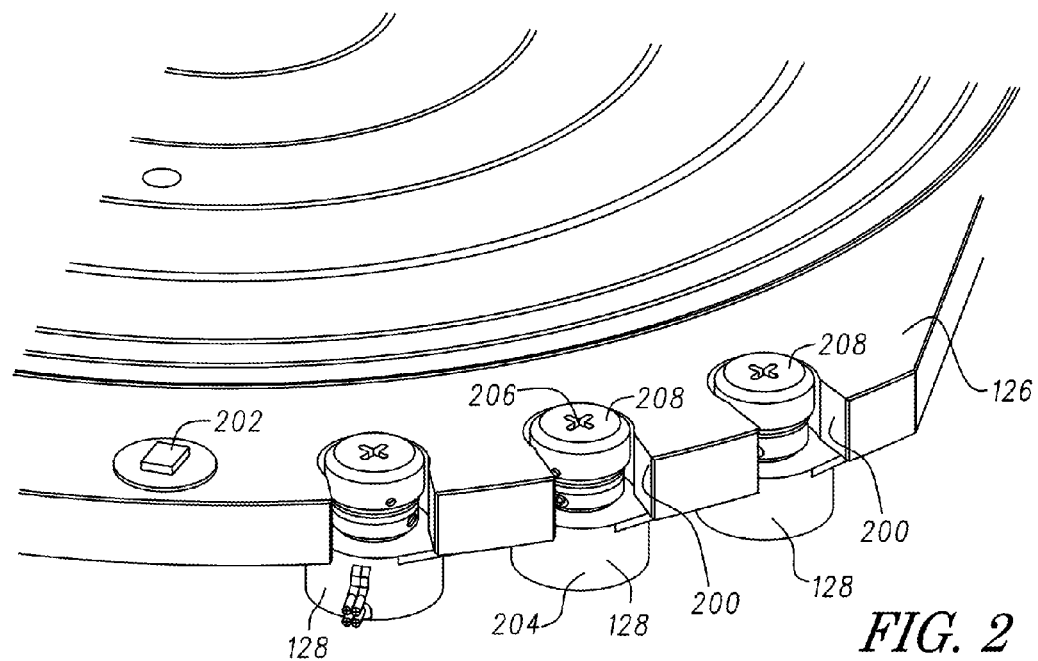
FIG. 2 is a detailed perspective view of one example of a sample stage including a stage receptacle flange and a plurality of probe change tools.

FIG. 2 shows a detailed perspective view of the stage receptacle flange 126 of the sample stage surface 112 (previously shown in FIG. 1). As shown in the example a plurality of probe change tools 128 are provided in corresponding stage receptacles 200. As shown in another stage receptacle 200 a diagnostic sample 202 is provided. In one example the diagnostic sample 202 is used to calibrate one or more of the testing instrument 102 (e.g., a transducer of the testing instrument), a probe installed in the testing instrument 102 or the like. For instance the diagnostic sample 202 includes a material such as aluminum, steel or the like having known mechanical or electrical characteristics. By testing the testing instrument 102 (and for instance a newly installed probe) on the diagnostic sample 202 the corresponding mechanical response of the testing instrument (of the transducer) as well as the characteristics of the probe (installed with the probe change tool 128) are ascertained and used to calibrate the testing instrument 102 according to the performance of the transducer and as well as the newly installed probe.

Referring again to FIG. 2, the probe change tool 128 is shown coupled with the stage receptacle flange 126. In the example provided in FIG. 2 each of the probe change tools 128 includes a motor 204 and a drive cap 208 coupled with the motor 204. In one example the motor 204 provides rotation in at least one direction to the drive cap 208. Rotation of the drive cap 208 as well as a probe assembly (including a probe receptacle and a probe received in the probe receptacle) rotates the probe and is used to install (or extract) the probe in the testing instrument 102 (for instance in a transducer of the testing instrument). The motor 204 of each of the probe change tools 128 is in one example a single-direction motor providing a constant specified torque. For instance, one of the probe change tools 128 is configured to provide an installation torque for a probe installed in the testing instrument 102 while another of the probe change tools 128 provides an extraction torque (a higher torque provided in an opposed direction) to thereby extract and install a probe from the testing instrument 102. In this manner the probe change tools 128 may be used in a cooperative fashion with one of the probe change tools 128 designated as an installation tool and another of the probe change tools 128 designated as an extraction tool. In still another example, each of the motors 204 of the probe change tools 128 are configured to provide bi-directional rotation. Accordingly each of the probe change tools 128 is provides both installation and extraction rotation for the corresponding installation and extraction of a probe from the testing instrument 102. Optionally, the motor 204 is configured to provide adjustable torques between the installation and extraction rotation directions (e.g., to gradually increase and decrease torque as needed to protect sensitive instruments, such as transducers).

In one example, the probe change tool 128 includes a torque limiting clutch positioned between the drive cap 208 and the motor 204. The torque limiting clutch is described herein. In one example the torque-limiting clutch includes an adjustable slipping interface configured to ensure the installation torque is limited and accordingly over-torquing of the probe and corresponding damage to a transducer of the testing instrument 102 is prevented. Conversely, in another example in an extraction rotating direction the motor 204 is configured to provide a higher torque (e.g., not limited by a torque limiting clutch) to ensure the extraction of a probe from the testing instrument 102.

Referring again to FIG. 2, as shown each of the probe change tools 128 has a common or consistent receptacle socket 206. For instance, the receptacle sockets 206 include a plurality of grooves provided at a common orientation (e.g., orthogonal to each other) to thereby allow for reception of a corresponding fitting for instance a fitting of a probe receptacle as described herein. In other examples, the receptacle socket 206 includes a shape configured to transmit rotation and provide a common interface to a probe receptacle such as, but not limited to, ovular, triangular, star-shaped, square-shaped, grooves or ridges or the like. The common receptacle socket 206 allows for the ready reception and rotation of a probe receptacle having a corresponding common and consistent socket fitting 308 (in FIG. 3). The probe change tools 128 with this common receptacle socket 206 are thereby able to perform one or more of installation or extraction of probes by way of a common probe receptacle received at the receptacle socket 206. As will be described herein in one example the probe receptacles include a common and consistent socket fitting 308 (in FIG. 3) sized and shaped for reception within the receptacle socket 206 common to each of the probe change tools 128. In contrast, probe retention recesses 310 of each of the probe receptacles are sized according to the probes received therein. The probe retention recesses 310 correspond to the size and shape of the respective probes stored in each of the probe receptacles. Accordingly, with the use of the probe change tools 128 shown in FIG. 2 as well as the probe receptacles (described herein) a variety of probe types having differing sizes and shapes may be installed in the testing instrument 102 by way of a common and consistent interface between the probe change tools 128 having the consistent receptacle sockets 206 and the corresponding probe receptacles 306 having varied probe retention recesses and common socket fittings.

Figure 3:
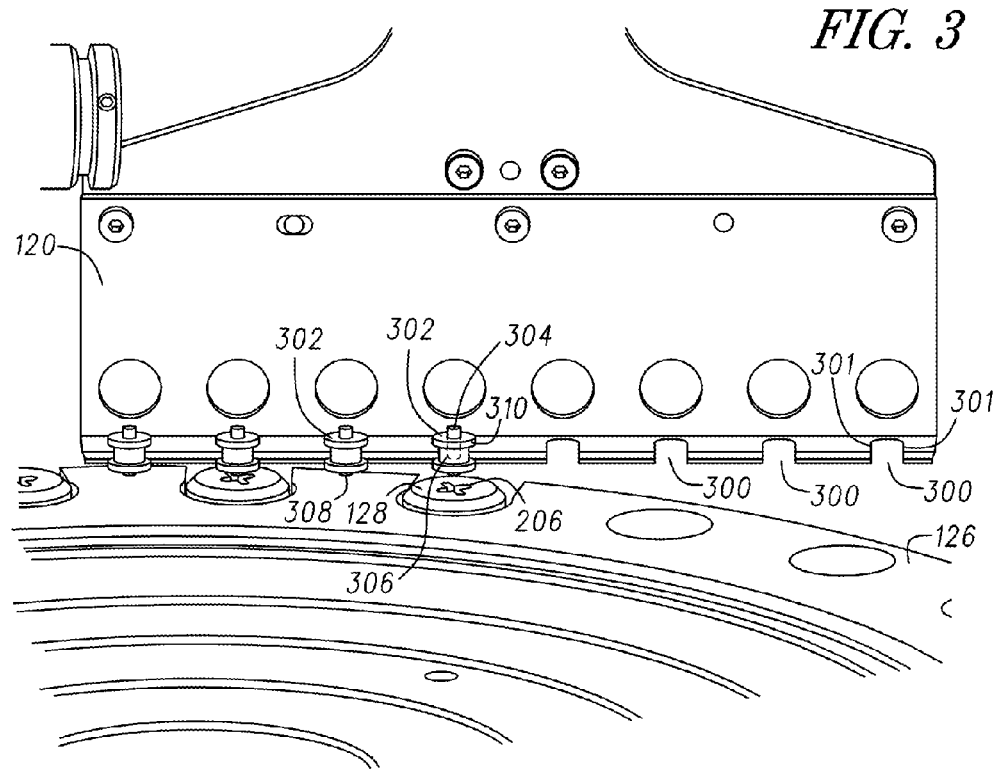
FIG. 3 is a detailed perspective view of one example of a probe magazine coupled with the instrument assembly with a probe change tool aligned with a probe assembly at a probe assembly station.

FIG. 3 shows a detailed perspective view of the probe magazine 120 positioned near the stage receptacle flange 126 and the probe change tools 128 coupled along the stage receptacle flange 126. As shown in FIG. 3, the probe magazine 120 includes a plurality of probe assembly stations 300 positioned along the probe magazine 120. For instance, in the example shown in FIG. 3 the probe magazine 120 includes eight separate probe assembly stations 300. As described herein the probe assembly stations 300 are configured to each hold a probe assembly 302. Examples of the probe assemblies 302 are provided in FIG. 3 and include a probe 304 received within a probe receptacle 306.

As previously described herein, in one example the probe receptacles 306 include a common consistent socket fitting 308 sized and shaped for corresponding reception and inter-fitting with the receptacle socket 206 of the probe change tools 128. The common interface between the socket fittings 308 and the corresponding receptacle sockets 206 allows for the installation of a plurality of differing probe types optionally having differing shapes and sizes into the testing instrument 102. As shown in FIG. 3, the probe receptacles 306 each include the previously described probe retention recesses 310. In one example the probe retention recesses 310 have shapes and sizes configured to receive a corresponding probe type. For instance, one of the probe receptacles 306 has a probe retention recess 310 having a first shape and size configured to hold a corresponding probe having a complimentary shape and size. While another of the probe receptacles 306 has a differing shape and size configured to hold a second type of probe 304 therein. The probes held within the probe receptacle 306 are provided in a 'probe down' fashion for instance with the tip of the probes provided within the probe receptacle 306 (e.g., in the probe retention recess 310).

Referring again to the probe magazine 120 shown in FIG. 3, the probe magazine 120 includes a plurality of probe assembly stations 300. In one example each of the probe assembly stations 300 includes corresponding handling prongs 301 sized and shaped to receive a probe receptacle 306 therein. The handling prongs 301 allow for the retention of the probe receptacle 306 and accordingly the probe assemblies 302 (including the probes 304 therein) at each of the probe assembly stations 300. The handling prongs 301 reliably position the probe receptacles 306 at indexed locations for probe changing (and storage) and thereby ensure that alignment is achieved between the probe change tool 128 and the socket fittings 308 of each of the probe receptacles 306 with operation of actuators, such as the stage actuators 114. For instance, as shown in FIG. 3 the probe change tool 128 is aligned with the probe assembly 302 provided at the fourth (from the left) probe assembly station 300. In one example, the probe assembly stations 300 are indexed, for instance by a controller of the instrument assembly 100, and thereby readily located with the stage actuators 114 moving the probe change tools 128 into one or more aligned configurations with each of the probe assembly stations 300. Similarly as probes are extracted from the testing instrument 102 the probe change tools 128 are readily aligned with empty probe assembly stations 300 to thereby position worn or differing probes (housed in probe receptacles 306) at each of the corresponding probe assembly stations 300. At a later time worn probes (as well as their probe receptacles 306) are removed and replaced with corresponding new probe assemblies 302 including new (or differently configured) probes 304 provided in the probe receptacles 306.

In yet another example, the probe magazine 120 is configured for instance in one or more of the probe assembly stations 300 to include diagnostic probes therein (as described previously). In one example, the diagnostic probes provide one or more weighted probes having known weight configured to provide a calibration function for the testing instrument 102. In one example the probe magazine 120 includes a first diagnostic probe provided in the probe assembly station 300 (designated as station seven counted from the left) and a second diagnostic probe having a differing weight at a second probe assembly station (for instance the eighth station counted from the left). The diagnostic probes are coupled with the testing instrument 102 in sequence to accordingly associate a known weight with the testing instrument 102 to allow for measurement of the mechanical response of the testing instrument 102. The mechanical responses measured with each of the diagnostic probes is accordingly used to provide a baseline for the mechanical response of the testing instrument 102 (the transducer of the testing instrument) to thereby calibrate the testing instrument 102 for future use.

Referring again to FIG. 3 in operation a probe change tool such as the probe change tool 128 along the stage receptacle flange 126 is aligned with the probe magazine 120. For instance, the probe change tool 128 is aligned with the fourth station of the probe assembly stations 300 as shown. In one example the probe magazine 120 is lowered to the probe change tool 128 with an actuator, such as the magazine actuator 122. In another example, the sample stage surface 112 including the probe change tool 128 is raised to the probe magazine 120 with a "z" actuator provided as one of the stage actuators 114. As the probe change tool 128 and the probe assembly station 300 are brought into proximity the socket fitting 308 (having a consistent configuration across each of the probe receptacles 306) is received by the receptacle socket 206. With the socket fitting 308 received by the receptacle socket 206 the probe assembly 302 at the desired probe assembly station 300 is coupled with the probe change tool 128. In one example, the stage actuator 114 (e.g., by way of translational movement) moves the probe change tool 128 outwardly from the probe magazine 120 and thereby decouples the probe assembly 302 from the handling prongs 301. After disengaging the probe receptacle 306 from the probe magazine 120 the probe magazine 120 is optionally raised or the sample stage surface 112 is lowered relative to the probe magazine 120 to ensure the probe change tool 128 is out of contact with the probe magazine 120. With the probe receptacle 306 coupled to the probe change tool 128 the probe change tool 128 is ready for installation of the associated probe 304 to the testing instrument 102 (after alignment to the probe change tool 128 with the testing instrument 102 as shown in FIG. 4).

Figure 4:
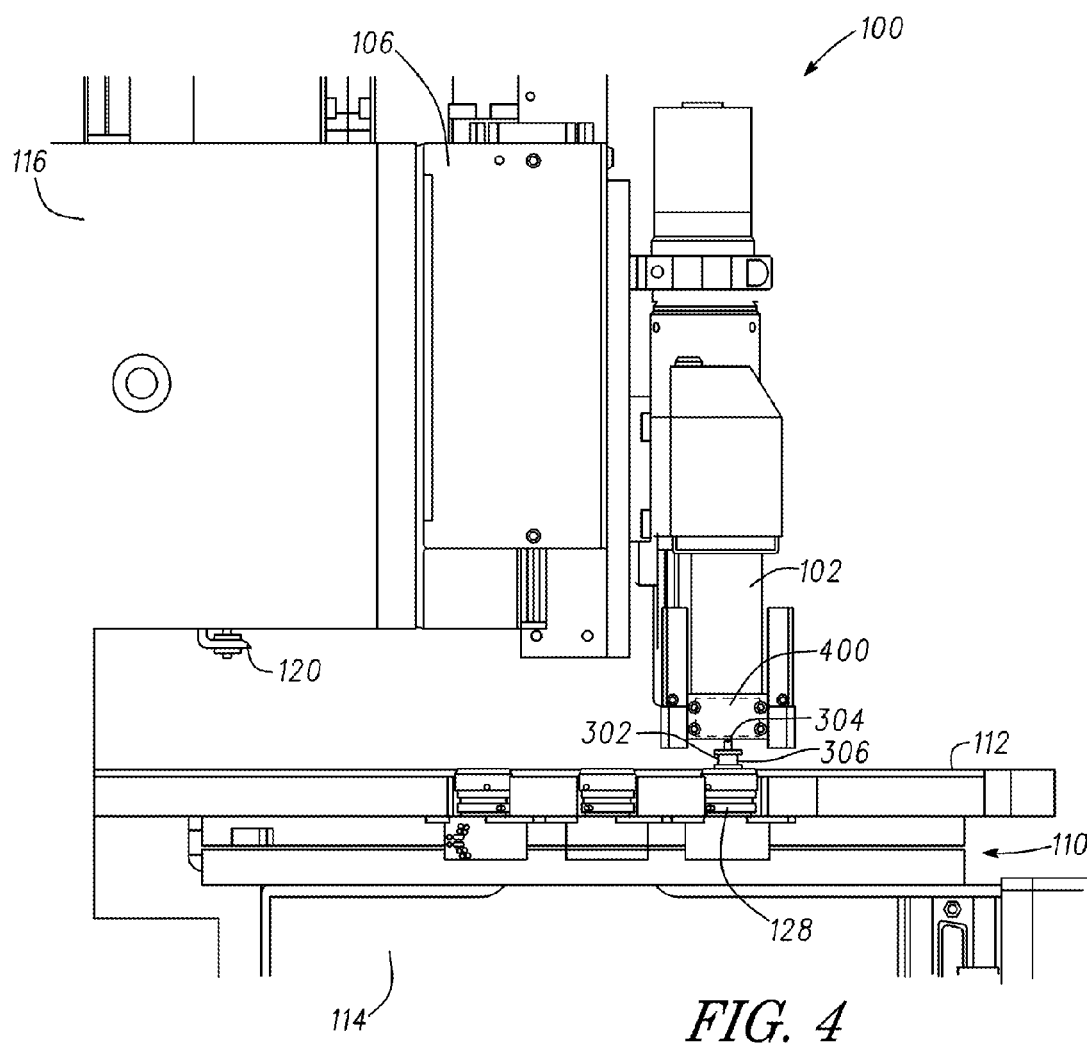
FIG. 4 is a side view of the instrument assembly of FIG. 1 with a probe assembly coupled with a probe change tool aligned with a transducer.

FIG. 4 shows the probe change tool 128 moved into alignment with the testing instrument 102. As shown, the probe change tool 128 and the probe assembly 302 thereon are aligned with the transducer 400 of the testing instrument 102. In one example the transducer 400 is a capacitive transducer including a plurality of capacitor plates. The probe 304 is coupled with a middle (movable) plate of the capacitive transducer 400. When installation is desired the aligned probe change tool 128 is raised or the testing instrument 102 is lowered relative to the probe change tool 128. Raising or lowering the corresponding components of the instrument assembly 100 accordingly moves the probe 304 into close proximity to transducer 400. The probe change tool 128 is operated to rotate the probe change tool 128 (the drive cap 208 having the receptacle socket 206 thereon). Rotation is transmitted through the receptacle socket 206 to the socket fitting 308 of the probe receptacle 306 and correspondingly transmitted to the probe 304 received in the probe retention recess 310 of the probe receptacle 306. Where the probe 304 and the transducer 400 include corresponding threads, interfitting surfaces or the like, rotation installs the probe 304 to the transducer 400.

In one example, the probe change tool 128 includes a torque limiting clutch as described herein. As a counter torque is transmitted through the probe 304 by tightening engagement with the transducer 400 the counter torque triggers the torque limiting clutch of the probe change tool 128 and allows for slippage between the drive cap 208 and the motor 204. Slipping between the drive cap 208 and the motor 204 substantially prevents over torquing of the probe 304 into the transducer and corresponding damage to the transducer is thereby substantially prevented.

After installation of the probe 304 into the transducer 400 of the testing instrument 102 the probe change tool 128 is withdrawn relative to the transducer 400. For instance, the probe receptacle 306 as well as the probe change tool 128 are lowered relative to the testing instrument 102 (in another example the testing instrument 102 is raised) to thereby disengage the probe receptacle 306 from the probe 304. The probe receptacle 306 is thereafter repositioned (e.g., with movement of the sample stage surface 112) to align the now empty probe receptacle 306 with a corresponding empty probe assembly station 300 (shown in FIG. 3). The empty probe receptacle 306 is thereafter stored at one of the probe assembly stations 300 for future use. In another example, where extraction of the probe 304 is needed (because of wear, the need for a differing probe type or the like) the probe receptacle 306 (empty from having had its probe installed previously) is coupled with the probe change tool 128 and aligned with the testing instrument 102 to accordingly extract the probe 304 therefrom.

For extraction the empty probe receptacle 306 is moved into alignment with the testing instrument 102 and one or more of the probe change tool 128 and the testing instrument 102 are moved to bring the testing instrument 102 into close positioning relative to the probe receptacle 306. The probe receptacle 306 receives the probe 304 (e.g., worn probe) therein. The probe change tool 128 rotates in an opposed direction to the installation direction and accordingly decouples the probe 304 from the testing instrument 102. The used probe 304 as well as the probe receptacle 306 are removed from the testing instrument 102 and in one example stored in the probe magazine 120 (see FIG. 3) in an empty probe assembly station 300.

In one example, the extraction torque used to decouple the probe 304 from the testing instrument 102 is a higher torque relative to the installation torque provided in an installation operation with the probe change tool 128. For instance, a torque limiting clutch is not activated with opposed rotation used during extraction. Accordingly, with a higher extraction torque the probe 304 is readily removed from the testing instrument 102. Because the probe 304 cannot be overtightened when extracted the higher torque is used to ensure removal of the probe 304 from the testing instrument 102.

Optionally, the transducer 400 of the testing instrument 102 is calibrated with one or more of the diagnostic probes as previously described herein. In such an example the installation and extraction of the diagnostic probes (e.g., diagnostic weights having differing and known weights) is conducted in substantially the same fashion relative to the installation or extraction of the probes 304 as described herein.

Figure 5A:
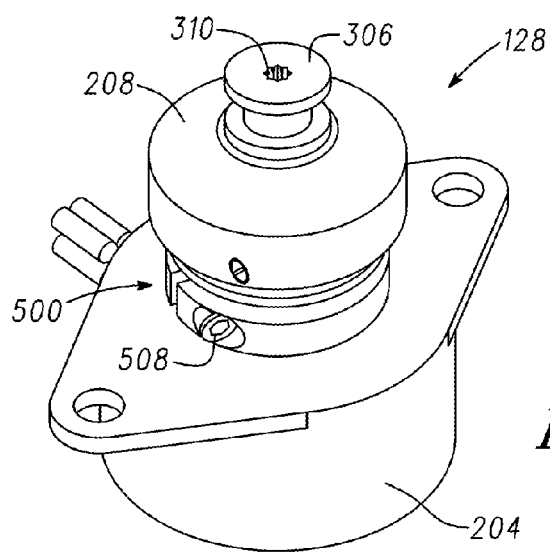
FIG. 5A is a perspective view of one example of a probe assembly coupled with a probe change tool.

FIG. 5A shows one example of a probe change tool, such as the probe change tool 128. As previously described herein, the probe change tool 128 is usable with a probe changing assembly such as the probe changing assembly 118 shown in FIG. 1. In another example, the probe change tool 128 is usable in another probe changing assembly such as the probe changing assembly 704 shown and described in FIG. 7. Referring again to FIG. 5A, the probe change tool 128 includes the motor 204 coupled with the drive cap 208. A probe receptacle 306 including a probe retention recess 310 sized and shaped for one or more types of probes is coupled with the drive cap 208. The motor 204 is configured to provide rotation to the drive cap 208 and corresponding rotation to the probe receptacle 306 and a probe (see probe 304 shown in FIG. 3) within the probe retention recess 310. In one example the motor 204 is configured to provide rotation in a single direction for instance in an installation or extraction direction for the probe 304. In another example the motor 204 provides bi-directional movement for instance rotation of the probe 304 in an installation direction as well as rotation of the probe 304 in an extraction direction for instance to remove the probe 304 from the testing instrument 102 such as the testing instrument shown in FIG. 4.

Optionally the probe change tool 128 includes a torque limiting clutch 500 as described herein. In one example the torque limiting clutch 500 is operable to provide a slipping interface between the drive cap 208 and the motor 204 to limit the amount of torque applied to the probe 304 and sensitive instruments, for instance in the installation direction. By limiting the amount of torque provided to the probe 304 in the installation direction a corresponding limit is provided for the application of torque to the transducer 400 shown in FIG. 4 and damage to the transducer 400 (e.g., over-rotation of a center plate of the transducer 400 relative to opposing plates) is thereby avoided. One example of the torque limiting clutch 500 is shown in FIG. 5B and described further herein.

Referring again to FIG. 5A, the drive cap 208 is shown coupled with the probe receptacle 306. As previously described, the probe receptacle 306 provides a common fitting and interface to facilitate the coupling of a probe 304 with the drive cap 208 for installation and extraction of the probe 304 from the testing instrument 102 shown in FIG. 4. The probe receptacle 306 provides a common interface between the drive cap 208 and the probe 304. Conversely the probe retention recess 310 provides a recess sized and shaped for the reception of a correspondingly sized and shaped probe 304 provided therein. Accordingly the probe receptacle 306 provides a common interface with the drive cap 208 while providing a customized recess sized and shaped for retention of one or more of a variety of different probe types therein. Accordingly, the probe change tool 128 is configured to couple with the consistent interface of the probe receptacle 306 and thereby install and extract one or more probes 304 optionally having a variety of sizes and shapes.

Figure 5B:
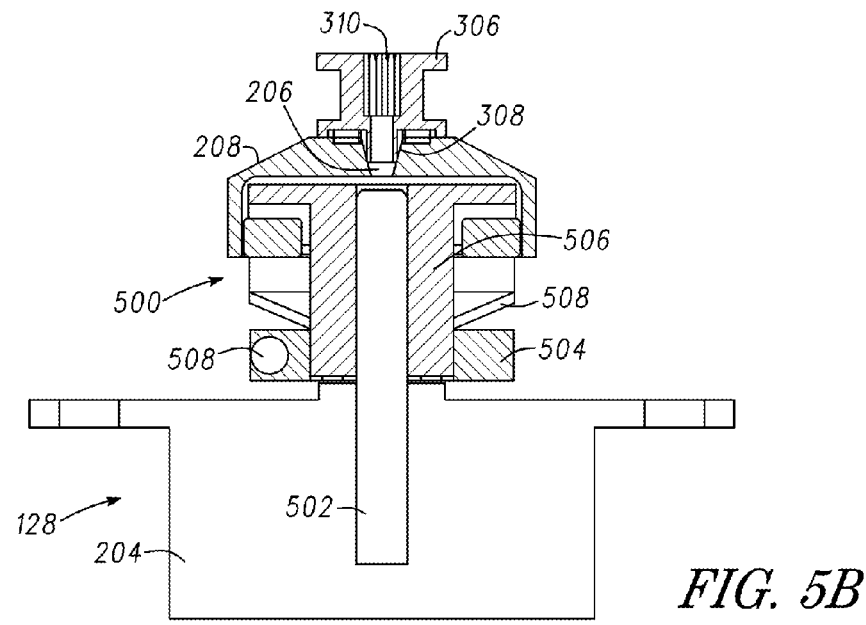
FIG. 5B is a cross sectional view of the probe assembly and probe change tool of FIG. 5A.

One example of a receptacle socket 206 for use with the probe receptacle 306 is shown in cross section in FIG. 5B. The socket fitting 308 of the probe receptacle 306 is correspondingly shaped and sized to the receptacle socket 206 of the drive cap 208. By aligning the socket fitting 308 with the receptacle socket 206 a common interface is provided between the drive cap 208 and the probe receptacle 306 and one more of installation and extraction rotation is transmitted to the probe receptacle 306 and to a probe 304 seated within the probe retention recess 310.

FIG. 5B is a cross sectional view of the probe change tool 128 previously shown for instance in FIG. 1 and further shown in FIG. 5A. One example of a torque limiting clutch 500 is shown in FIG. 5B. The torque limiting clutch 500 provides an intermediate interface between a motor shaft 502 and the drive cap 208. For instance the torque limiting clutch 500 includes a ring clamp 504 extending around a clutch sleeve 506. The clutch sleeve 506 is in one example fixedly coupled with the drive cap 208 and selectively slidably coupled with the motor shaft 502. Tightening of the ring clamp 504 with a fastener such as the ring fastener 508 tightens the clutch sleeve 506 around the motor shaft 502 and provides selective gripping and slipping engagement between the motor shaft 502 and the clutch sleeve 506. As a sufficient counter torque is provided to the drive cap and the clutch sleeve 506 208 (e.g., as the probe 304 is tightened into the transducer 400) the friction fitting between the clutch sleeve 506 and the motor shaft 502 is overcome to allow the drive cap 208 and clutch sleeve 506 to slip relative to the motor shaft 502 (that continues to turn). One example of the ring fastener 508 includes a set screw such as the set screw 508 shown in FIGS. 5A and 5B. In one example the ring clamp 504 includes counter-threaded openings at each of the ends of the ring clamp 504 to thereby allow tightening or loosening of the ring fastener 508 and corresponding tightening or loosening of the ring clamp 504 around the clutch sleeve 506. In one example, the ring fastener 508 is graduated so a corresponding number of rotations or partial rotations of the ring fastener 508 provides a corresponding clutching engagement between the motor shaft 502. For instance, with a set number of turns of the ring fastener 508 a corresponding counter torque will cause the clutch sleeve 506 to overcome the frictional engagement between the clutch sleeve 506 and the motor shaft 502 to accordingly allow slipping between the drive cap 208 and the motor shaft 502.

In another example, the torque limiting clutch 500 includes a bevel clamp 508 used in cooperation with the ring clamp 504. The bevel clamp 508 as shown in FIG. 5B has a taper at least partly received between the ring clamp 504 and the clutch sleeve 506. Tightening of the ring clamp 504 accordingly tightens the bevel clamp 508 and thereby further tightens the clutch sleeve 506. Stated another way, the ring clamp 504 and the bevel clamp 508 cooperate to tighten the clutch sleeve 506 around the motor shaft 502 to provide a selective slipping interface between the motor shaft 502 and the clutch sleeve 506.

In one example, two probe change tools 128 are used for extraction and installation of probes 304. The torque limiting clutch 500 of the installation tool 128 is configured to provide a slipping engagement at a lower counter torque relative to the torque limiting clutch 500 of the extraction tool 128. For instance, the ring clamp 504 (and the optional bevel clamp 508) is tightened to a lesser extent for the installation probe change tool 128 compared to the extraction probe change tool 128 (e.g., the ring clamp 504 is tightened to a greater extent for the extraction tool). Accordingly the installation probe change tool 128 provides a slipping engagement between the motor shaft 502 and the drive cap 208 at a lower torque during installation while the extraction probe change tool 128 provides slipping engagement at a relatively higher torque because the risk of over tightening the probe 304 and correspondingly damaging the transducer 400 is minimized during extraction (relative to installation). By including a torque limiting clutch 500 with the extraction probe change tool 128 even minimal risk of damage to the transducer 400 during extraction is further reduced.

Figure 6A:
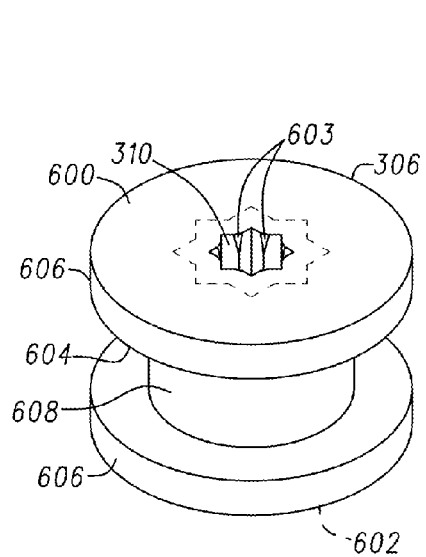
FIG. 6A is a perspective top view of one example of a probe receptacle including a probe retention recess.
Figure 6B:
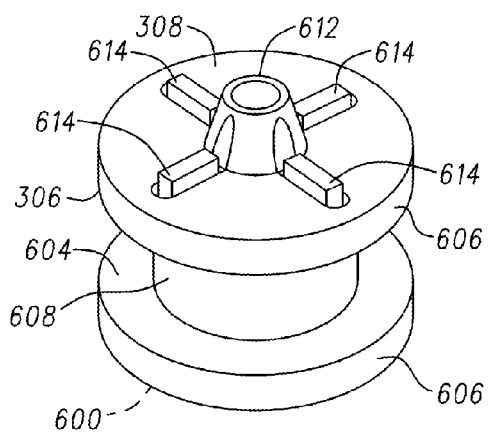
FIG. 6B is a perspective bottom view of the probe receptacle of FIG. 6A including a socket fitting.

FIGS. 6A and 6B show one example of a probe receptacle 306. The probe receptacle 306 includes a probe face 600 including the probe retention recess 310 and a socket face 602 including the socket fitting 308. Referring first to FIG. 6A, the probe retention recess 310 is shown with an exemplary star configuration sized and shaped for the reception of a correspondingly sized and shaped probe 304 therein. As previously described herein, the probe retention recess 310 is varied to accordingly provide a recess sized and shaped for the reception and snug retention of like sized and shaped probes 304 therein. In one example, the probes 304 vary by one or more of shape, size or the like. In still another example the probes 304 vary by other characteristics including but not limited to, the material of probe construction, the probe function (e.g., as a pushing or pulling probe, scratch probe, indentation probe or the like).

As shown in FIG. 6A, the exemplary probe receptacle 306 includes a star-shaped probe retention recess 310. The star shaped probe retention recess 310 corresponds to the shape of the probe 304 received, as described herein. In one example the probe 304 has an identical shape to the probe retention recess 310. In another example, the probe 304 has a corresponding shape to the probe retention recess 310 according to correspondence of a subset of corners, grooves, ridges or the like between the probe and the recess. For instance, an exemplary probe 304 has a square shape and the corners of the square shape correspond to a subset of corners (grooves) of the star shaped probe retention recess 310 (e.g., the star shape is formed by two squares matching the shape of the probe and rotated 45 degrees relative to each other). As shown in the example provided in FIG. 6A the probe retention recess has eight corners (grooves). By seating a corresponding square shaped probe 304 in the probe retention recess 310 the four corners of the probe 304 readily fall into a subset of four corresponding corners of the recess 310 as the probe is seated in the recess (e.g., during extraction). Stated another way, the probe 304 readily 'jogs' relative to the probe retention recess 310 during reception because of the plurality of corners (grooves) of the recess 310 greater than the number of corresponding corners of the probe 304, and thereby minimizes any chance of misalignment between the probe and the recess. In still another example, the probe retention recess 310 optionally includes tapers 603 to facilitate the reception of the probe 304 within the recess 310. As the probe 304 is lowered into the recess 310 the tapers 603 guide the probe 304 into a seated position aligned with the corresponding features of the recess 310.

One example of a variation of the probe retention recess 310 is provided in dashed lines in FIG. 6A for reception of a larger probe 304. In other examples, the probe retention recess 310 has a square or diamond-shaped recess shape, an ovular shape or the like that is complementary and configured for snug reception of a corresponding probe 304 therein and transmission of rotation from the probe receptacle 306 to the probe 304 (e.g., for installation within the transducer 400) of the testing instrument 102, as shown in FIG. 4. The probe retention recess 310 shown in FIG. 6A is sized and shaped to receive the tip of a probe therein. Accordingly, the installation end of the probe extends out of the probe retention recess 310 for installation within the corresponding socket of the transducer 400 of the testing instrument 102.

As further shown in FIG. 6A the probe receptacle 306 includes one or more flanges 606 and a neck 608 extending between the flanges 606. In one example, one or more of the flanges 606 in cooperation with the neck 608 provides a handling surface 604. In one example the handling surface 604 is a consistent handling surface mirrored between a plurality of probe receptacles 306. The handling surface 604 is thereby easily inter-fit with and interacted with by the handling prongs 301 of the probe magazine 120 shown in FIG. 3. Accordingly a plurality of varying probes 304 (varied in size, shape or the like) are retained by the probe receptacles 306 and then held at consistent probe assembly stations 300 with the handling prongs 301 as shown in FIG.

3. The probe receptacles 306 are held at the probe assembly stations 300 by the handling surfaces 604. The handling prongs 301 and the handling surfaces 604 are further used to position the probe receptacles 306 (and probes 304) relative to one or more of the probe change tools 128. For instance as shown in FIG. 1 the probe magazine 120 is moved by a magazine actuator 122 or is held in place and stage actuators 114 move the probe change tools 128 into alignment with one or more of the probe assembly stations having a probe receptacle 306 and a probe 304 therein. After alignment and coupling of the probe receptacle 306 with the probe change tool 128 the probe magazine 120 or the sample stage surface 112 including the probe change tools 128 thereon is moved relative to the handling prongs 301 to decouple the probe receptacle 306 from the probe assembly station 300 and thereafter allow for installation of a probe 304 into the testing instrument 102.

FIG. 6B shows the opposed socket face 602 of the probe receptacle 306. The socket face 602 includes the socket fitting 308. As shown the socket fitting 308 includes an optional alignment pin 612 and a plurality of drive flanges 614. The probe receptacle 306 is in one example one of a plurality of probe receptacles 306 sized and shaped for retention within a probe magazine 120. The socket fitting 308 provides a consistent interface with the probe change tool 128 for instance with the receptacle socket 206 of the probe change tool as previously described herein. In operation, the probe receptacle 306 in the probe magazine 120 is aligned with the receptacle socket 206 of the probe change tool 128. In one example, the probe change tool 128 is moved into alignment with the probe receptacle 306 to thereby align the alignment pin 612 with the receptacle socket 206. In another example, the probe magazine 120 is moved relative to the probe change tool 128. Alternatively, there is some combination of movement of the probe change tool 128 and the probe magazine 120 to align the receptacle socket 206 with the alignment pin 612. As the alignment pin 612 is aligned with the receptacle socket 206 the elevation between the probe receptacle 306 and the probe change tool 128 is decreased to seat the alignment pin 612 within the receptacle socket 206. As the probe receptacle 306 is seated within the receptacle socket 206 the drive flanges 614 either naturally fall into corresponding grooves of the receptacle socket 206 or have one or more features configured to facilitate the reception of the drive flanges 614 within the corresponding grooves of the receptacle socket 206. For instance the drive flanges 614 include one or more bevels, tapers or the like configured to ensure reception of the probe receptacle 306 in the receptacle socket 206 in another example the drive flanges 614 (and optionally the alignment pin 612) are magnetic and thereby configured to naturally bias themselves into corresponding ferrous portions of the receptacle socket 206 (ferrous portions at the bottom or within the grooves of the receptacle socket 206). The magnetic drive flanges 614 further retain the probe receptacle 306 to the receptacle socket 206 and the probe change tool 128 (as a single cohesive unit) during rotation of the probe change tool and movement of the assembly of the tool 128 and the probe assembly 302 (e.g., the probe 304 and the receptacle 306), for instance between the probe magazine 120 and the testing instrument 102.

The socket fitting 308 including the alignment pin 612 and the drive flanges 614 cooperate to provide reliable and consistent positioning of the probe receptacle 306, and correspondingly the probe 304 housed therein, relative to the probe change tool 128 (and the transducer 400 when the probe receptacle 306 and the probe 304 coupled with the probe change tool 128 are aligned with the transducer). Accordingly, misalignment of the probe 304 relative to the probe change tool 128 and the transducer 400 is substantially minimized with the consistent inter-fitting of the socket fitting 308 with the receptacle socket 206 when used with the probe changing assembly 118. Accordingly, with the probe receptacle 306, the common interface provided by the receptacle, the probes 304 received within the corresponding probe retention recesses 310 the probe changing assembly 118 is configured to install and extract a variety of probes having differing sizes and shapes from a single instrument such as the testing instrument 102. Misalignment between a variety of probe shapes is substantially avoided by using a consistent probe receptacle 304 having a correspondingly consistent socket fitting 308 to thereby provide a common interface with the probe change tool 128.

FIG. 7 shows another example of an instrument assembly 700 including another example of a probe changing assembly 704. At least some of the components of the instrument assembly 700 are similar to the components of the instrument assembly 100 previously shown in FIG. 1 and described herein. For instance, the instrument assembly 700 includes an instrument assembly base 116. A sample stage assembly 110 is coupled with the instrument assembly base 116 and a sample stage surface 702 of the assembly 110 is coupled to the assembly base 116 with one or more stage actuators 114. In one example the stage actuators 114 provide one or more axes of movement, for instance "x," "y", "z" movement for the sample stage surface 702. In yet another example, the stage actuator 114 includes a rotatable (θ) actuating stage configured to rotate the sample stage surface 702 relative to the remainder of the instrument assembly 700 (including for instance the testing instrument 102).

As further shown in FIG. 7, the instrument assembly 700 includes a testing instrument 102 coupled to the instrument assembly base 116. As shown in FIG. 7 the instrument assembly base 116 extends (as an arch) over top of the sample stage assembly 110 to position the testing instrument 102 (e.g., on a primary instrument mount) relative to the sample stage surface 702. In one example, the testing instrument 102 includes a transducer configured to move a probe relative to one or more samples positioned on the sample stage surface 702. For instance, the testing instrument 102 is configured for one or more testing schemes including, but not limited to indentation, pushing (compression loading), pulling (tension loading), scratching, electrical characteristic testing or the like. In one example, the testing instrument 102 includes a transducer, such as the transducer 400 shown in FIG. 4, coupled with a probe extending from the testing instrument 102 and configured to test a sample on the sample stage surface 702. In the example shown in FIG. 7, an optional optical instrument 104 is provided adjacent to the testing instrument 102. The optical instrument 104 provides a visual means for identifying a testing location on a sample positioned on the sample stage surface 702. The spacing between the optical instrument 104 and the testing instrument 102 (the probe of the testing instrument) is a known distance. Accordingly, once a testing location is identified with the optical instrument 104 one or more of the testing instrument 102 or the sample stage surface 702 is moved relative to the optical instrument 104 to accordingly align the testing instrument 102 with the identified testing location.

As further shown in FIG. 7 the instrument assembly 700 includes an instrument changing assembly, such as a probe changing assembly 704. As shown the probe changing assembly 704 includes at least some components also found with the probe changing assembly 118 previously shown and described in FIG. 1. For instance, the probe changing assembly 704 includes a probe magazine 706 coupled with the instrument assembly base 116 (e.g., an instrument mount for the testing instrument 102). In one example, the probe magazine 706 is statically mounted to the instrument assembly base 116 and thereby retained in a desired position relative to the remainder of the probe changing assembly 704 including one or more probe change tools 128. In another example the probe magazine 706 includes a dedicated probe actuator such as the magazine actuator 122 shown in FIG. 1. The magazine actuator 122 allows for the positioning of the probe magazine 706 relative to the probe change tools 128. The probe magazine 706 includes a plurality of probe assembly stations similar in at least some regards to the probe assembly stations 300 of the probe magazine 120 shown in FIG. 3. For instance, each of the assembly stations is configured to hold a probe assembly including a probe receptacle having a probe received therein.

As further shown in FIG. 7 the probe changing assembly 704 includes one or more mechanisms to move probe change tools 128 relative to the sample stage surface 702 and the testing instrument 102 as well as the probe magazine 706. For instance as shown the probe changing assembly 704 includes a movable arm (e.g., a telescoping arm 708) and one or more probe change tools 128 provided at an end of the telescoping arm 708. As will be described herein in one example the probe changing tools 128 are substantially identical. For instance each of the probe changing tools is configured to provide one or both of installation rotation as well as extraction rotation. In another example, one of the probe change tools 128 is configured to provide an extraction rotation and the other of the probe change tools 128 is configured to provide an installation rotation. In one example the installation rotation applies limited torque to a probe coupled with a testing instrument 102 to thereby prevent overtorquing of the testing instrument 102 including any sensitive electronics such as capacitors therein.

In operation, the telescoping arm 708 allows for the positioning of the probe changing tools 128 relative to the probe magazine 706 and the testing instrument 102. Stated another way, the telescoping arm 708 provides a mechanism to move the probe changing tools 128 and probe assemblies coupled with the probe change tools 128 between the probe magazine 706 and the testing instrument 102.

As will be described herein, in one example the telescoping arm 708 is movable relative to an arm base with an actuator coupled between the arm base and the telescoping arm 708. In another example, a passive element is included with the telescoping arm to facilitate movement of the telescoping arm. For instance, in one example, the telescoping arm includes an arm lug. A lug anchor is provided with the remainder of the instrument assembly 700 (e.g., coupled with the instrument assembly base 116). The arm lug is coupled with the lug anchor when movement of the telescoping arm 708 and the probe change tools 128 thereon is desired. In the view shown in FIG. 7 the telescoping arm 708 is provided in a substantially withdrawn or retracted position. As shown, the probe change tools 128 are positioned away from a position overlying the sample stage surface 702. Accordingly the usable area of the sample stage surface 702 is maximized through retraction of the probe change tools 128. When extraction or installation of a probe to the testing instrument 102 is desired the telescoping arm 708 is deployed (e.g., over top of a portion of the sample stage surface 702) to provide access to the probe magazine 706 and the testing instrument 102.

Figure 8:
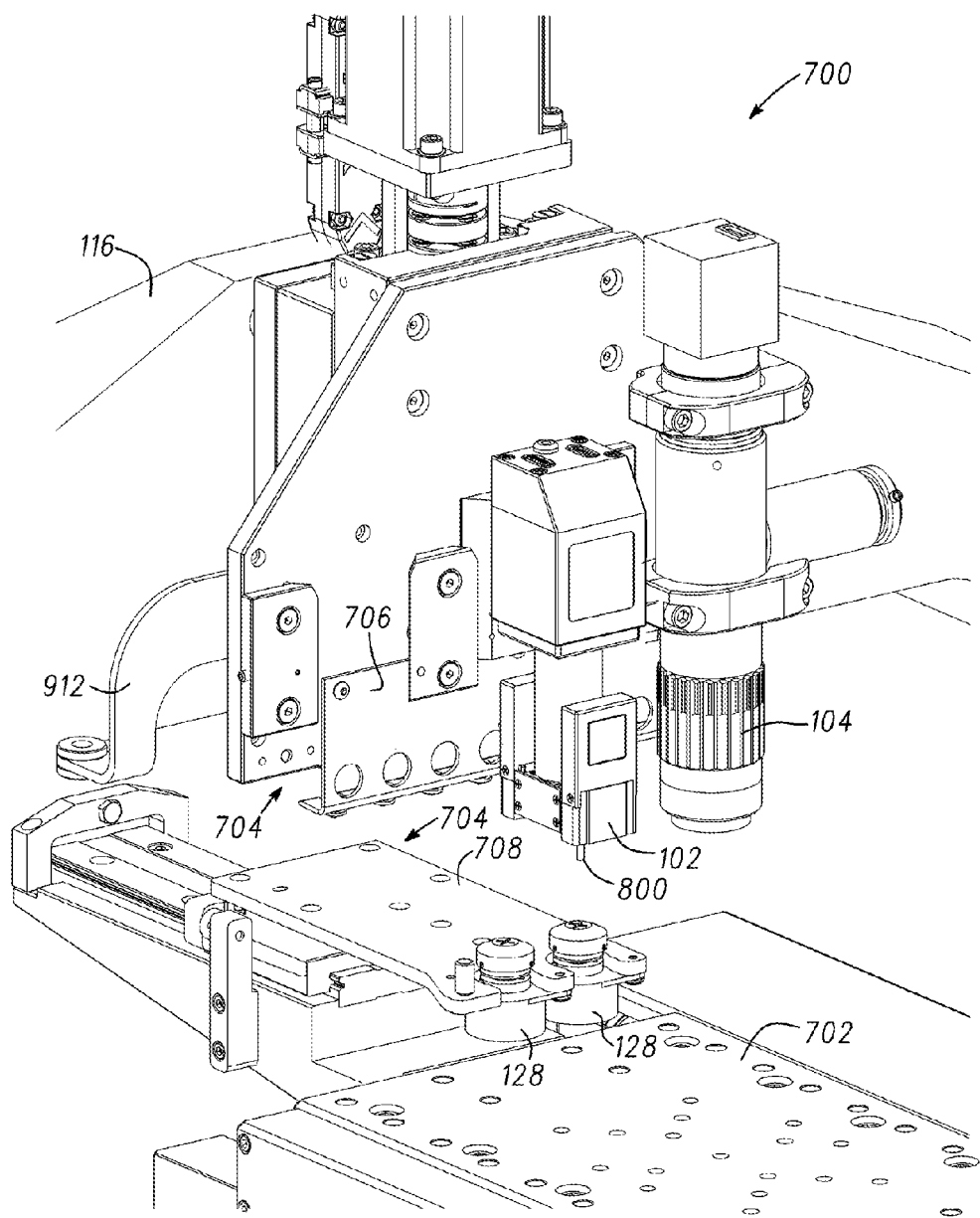
FIG. 8 is a detailed perspective view of the instrument changing assembly having a telescoping arm in a deployed position.

FIG. 8 shows the probe changing assembly 704 in a deployed configuration. The telescoping arm 708 is deployed relative to the remainder of the probe changing assembly 704 (including an arm base coupled with a telescoping arm). As shown, one of the probe change tools 128 is aligned with a probe 800 of the testing instrument 102. As further shown in FIG. 8, the telescoping arm 708 is deployed over a portion of the sample stage surface 702. That is to say a portion of the telescoping arm 708 including the probe change tools 128 thereon is co-extensive or aligned with a portion of the sample stage surface 702. By providing the probe changing assembly 704 over top of a portion of the sample stage surface 702 the overall footprint of the instrument assembly 700 is minimized. For instance, as extraction and installation of a probe is desired a portion of the probe changing assembly 704 including the telescoping arm 708 and the probe change tools 128 is positioned over top of the sample stage surface 702 on an as-needed basis to thereby allow for extraction and installation of probes with the testing instrument 102. When installation and extraction of probes is no longer desired, for instance after installation and calibration of a probe with the testing instrument 102, the telescoping arm 708 is retracted into the configuration shown in FIG. 7. Accordingly, the sample stage surface 702 is fully revealed thereby allowing access by the testing instrument 102 to substantially the entire sample stage surface 702.

Figure 9A:
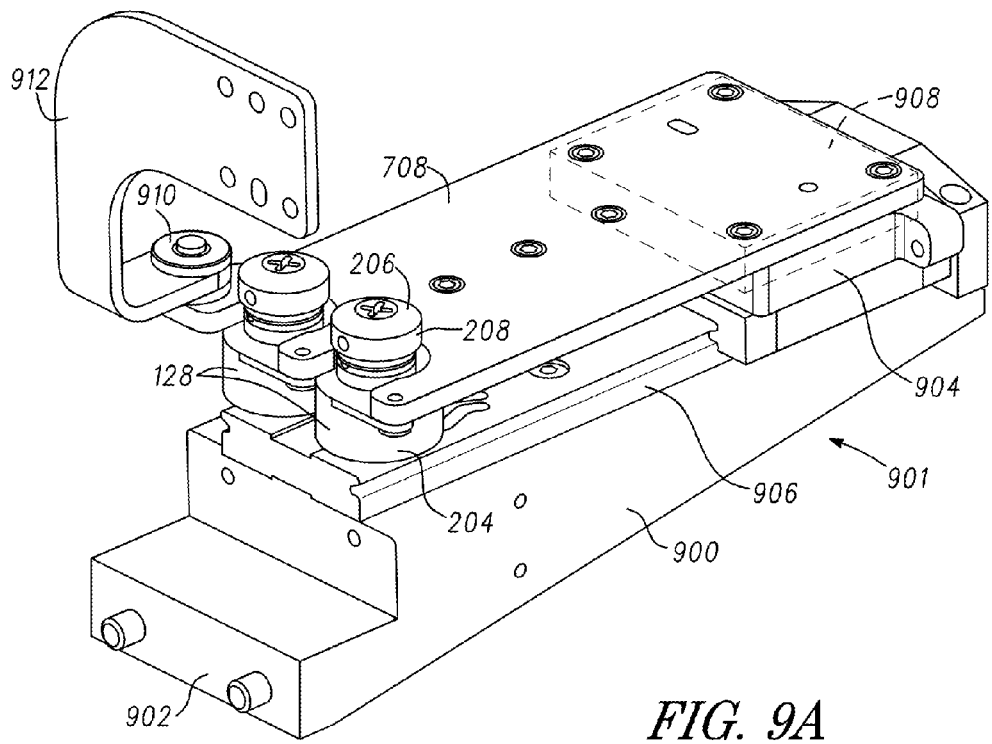
FIG. 9A is a perspective view of the telescoping arm in a retracted position with an arm lug coupled with a lug anchor of the instrument assembly.

FIG. 9A shows one example of an arm assembly 901 of the probe changing assembly 704. As shown, the arm assembly 901 includes the telescoping arm 708 movably (telescopically) coupled with an arm base 900. A carriage 904 provides the moving interface between the arm base 900 and the telescoping arm 708. The carriage 904 is optionally movable with the telescoping arm 708 along one or more carriage rails 906 provided along the arm base 900. The telescoping arm 708 as described in an example herein is shown with an elongate beam extending from the carriage 904 to the probe change tools 128. In another example, the telescoping arm 708 is a multi-member arm. Each of the members of the telescoping arm 708 moves independently (e.g., according to dedicated actuators) or as a unit in the manner of a multi-member arm that extends in a staggered telescoping fashion.

As described herein in one example the telescoping arm 708 is provided with a pulling lug 910. The pulling lug 910 in one example includes a post provided at an end of the telescoping arm 708 adjacent to the probe change tools 128. As shown in FIG. 9A, the pulling lug 910 is received within a corresponding portion of the lug anchor 912. As shown in FIGS. 7 and 8 the lug anchor 912 is coupled with a portion of the instrument assembly 700. For instance the lug anchor 912 is coupled with an instrument mount (also coupled with the testing instrument 102) and the lug anchor is movable with the instrument actuator 106. In another example, the lug anchor 912 is coupled with the instrument assembly base 116. With the lug anchor 912 coupled with the instrument actuator 106 the lug anchor 912 is movable vertically (e.g., up and down) relative to the pulling lug 910 to position the lug anchor 912 around the pulling lug 910.

In yet another example the arm assembly 910 includes an arm actuator (shown in dashed lines in FIG. 9A) coupled between the telescoping arm 708 and the arm base 900. In one example, the arm actuator 908 is configured to provide incremental precise movement of the telescoping arm 708 to thereby accurately position the probe change tools 128 relative to one or more of the probe magazine 706 and the testing instrument 102. For instance, in one example the arm actuator 908 includes but is not limited to a piezo actuator configured to walk or incrementally move the telescoping arm 708 (e.g., the carriage 904 coupled with the arm) relative to the arm base 900.

As further shown in FIG. 9A the arm assembly 901 includes an optional stage interface 902. Where the arm assembly 901 is coupled with the sample stage assembly 110 the stage interface 902 provides a solid coupling between the assembly 901 and the assembly 110. In one example, the stage interface 902 includes one or more pins, fasteners, interfittings, bayonets or the like to fixably couple the arm base 900 relative to the sample stage assembly 110 and thereby ensure a rigid coupling configured to ensure the precise correspondence of movement between the sample stage assembly 110 and the arm assembly 901, for instance through operation of the stage actuators 114. That is to say in one example the stage actuators 114 of the sample stage assembly 110 provide movement for the arm assembly 901 and the sample stage surface 702 as a unitary assembly to facilitate the movement of the telescoping arm 708 between the retracted and deployed positions as well as movement of the deployed probe change tools 128 relative to the probe magazine 706 and the testing instrument 102.

Figure 9B:
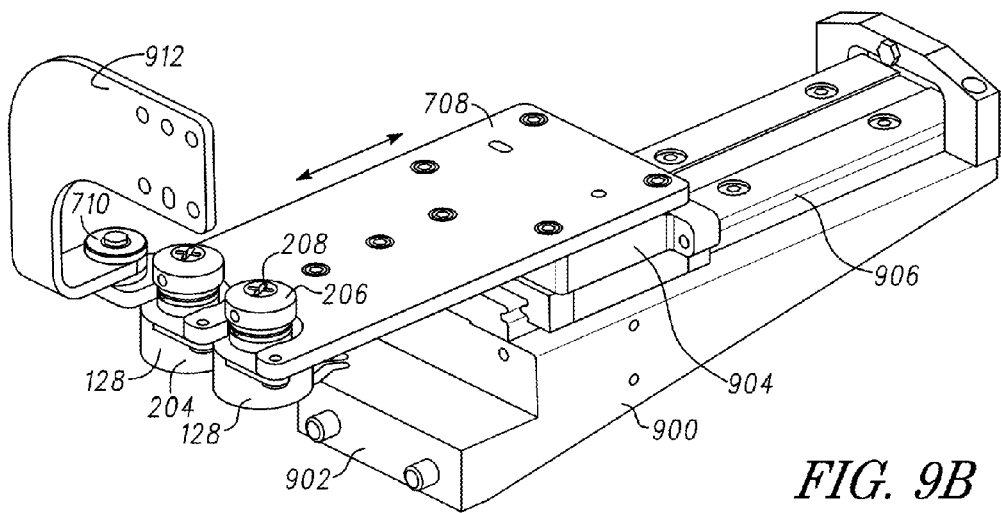
FIG. 9B is a perspective view of the telescoping arm in the deployed position with the arm lug coupled with the lug anchor.

Operation of the arm assembly 901 of the probe changing assembly 704 is shown in FIGS. 9A and 9B. The telescoping arm 708 is shown in the retracted position in FIG. 9A and in the deployed position in FIG. 9B. As shown in FIG. 9A, the pulling lug 910 is received within the lug anchor 912. As previously described herein in one example the instrument actuator 106 of the instrument assembly 700 lowers the lug anchor 912 (e.g., including an orifice therein) over top of the pulling lug 910 and seats the pulling lug within the anchor 912. In another example, the stage actuators 114 for instance a "z" actuator of the sample stage assembly 110 raises the pulling lug 910 into receipt with the lug anchor 912. After coupling between the lug anchor 912 and the pulling lug 910 (through inter-fitting of these features) the sample stage surface 702 of the sample stage assembly 110 is moved with the stage actuators 114. That is to say, as shown in FIG. 7 the sample stage surface 702 is moved into the page, for instance from right to left, to thereby move the arm base 900 in a corresponding fashion while the telescoping arm 708 is held static by the lug anchor 912. The telescoping arm 708 will accordingly deploy (remain static relative to the moving arm base 900) with the carriage 904 and thereby extend over at least a portion of the sample stage surface 702. Optionally, with the arm actuator 908 the telescoping arm 708 is deployed through the operation of the actuator 908 (e.g., a piezo actuator).

Referring again to the example where the lug anchor 912 is used to move the telescoping arm 708, after deployment of the telescoping arm 708 the lug anchor 912 is disengaged from the pulling lug 910 by relative movement (e.g., elevation) between the lug anchor 912 and the pulling lug 910. The stage actuators 114 are then operated to move the deployed telescoping arm 708 and the probe change tools 128 thereon relative to both the probe magazine 706 and the testing instrument 102 (e.g., coupled with instrument assembly base 116). For instance, the stage actuators 114 align one or more of the probe change tools 128 with a probe assembly of the probe magazine 706 and thereafter couple the probe assembly with the probe change tool 128 at a receptacle socket 206 (e.g., part of the drive cap 208). The probe change tool 128 is then moved (e.g., by the stage actuators 114) to align the probe change tool with the testing instrument 102. In a manner similar to the previously described probe changing assembly 118 alignment of the receptacle socket 206 and the probe assembly with the testing instrument 102 facilitates the installation of the probe of the probe assembly into the testing instrument 102. For example, the probe change tool rotates the probe in an installation direction to couple the probe to the testing instrument 102 (e.g., the transducer 400). Optionally, the probe change tool 128 includes a torque limiting clutch (e.g., clutch 500 described herein) that limits rotational torque transmitted to the transducer at the testing instrument 102 to substantially minimize the chance of damage to the testing instrument 102.

In another example in the deployed configuration shown in FIG. 9B the probe change tool 128 includes a probe receptacle 306 (e.g., without a probe 304) positioned on the receptacle socket 206 and is used to extract a probe from the testing instrument 102. The probe is extracted from the testing instrument 102 once the probe becomes degraded, worn, a probe with differing capabilities is desired or the like. In such an example the probe change tool 128 in the deployed configuration is moved into alignment with the testing instrument 102 (with the stage actuators 114) and the probe change tool 128 extracts the probe with rotation counter to an installation direction from the testing instrument 102. In another example, the other of the probe change tools 128 includes a replacement probe 304 in a probe receptacle 306 already positioned in the receptacle socket 206 (previously loaded from the probe magazine 706). The other probe change tool 128 is immediately moved into alignment with the now empty testing instrument 102 to install the new probe 304 into the testing instrument 102.

After completion of one or more of extraction or installation of a probe 304 with the testing instrument 102 the telescoping arm 708 is moved to the retracted position. In one example, the lug anchor 912 is aligned with the pulling lug 910 and coupled with the lug. The telescoping arm 708 is moved into the retracted position (see FIG. 9A) by relative movement between the arm base 900 and the telescoping arm 708 with the stage actuators 114. After moving of the telescoping arm 708 into the retracted position the lug anchor 912 is decoupled from the pulling lug 910. Optionally, the arm actuator 908 is used to move the telescoping arm 708 and the probe change tools 128 into the withdraw position from the deployed position.

Figure 10:
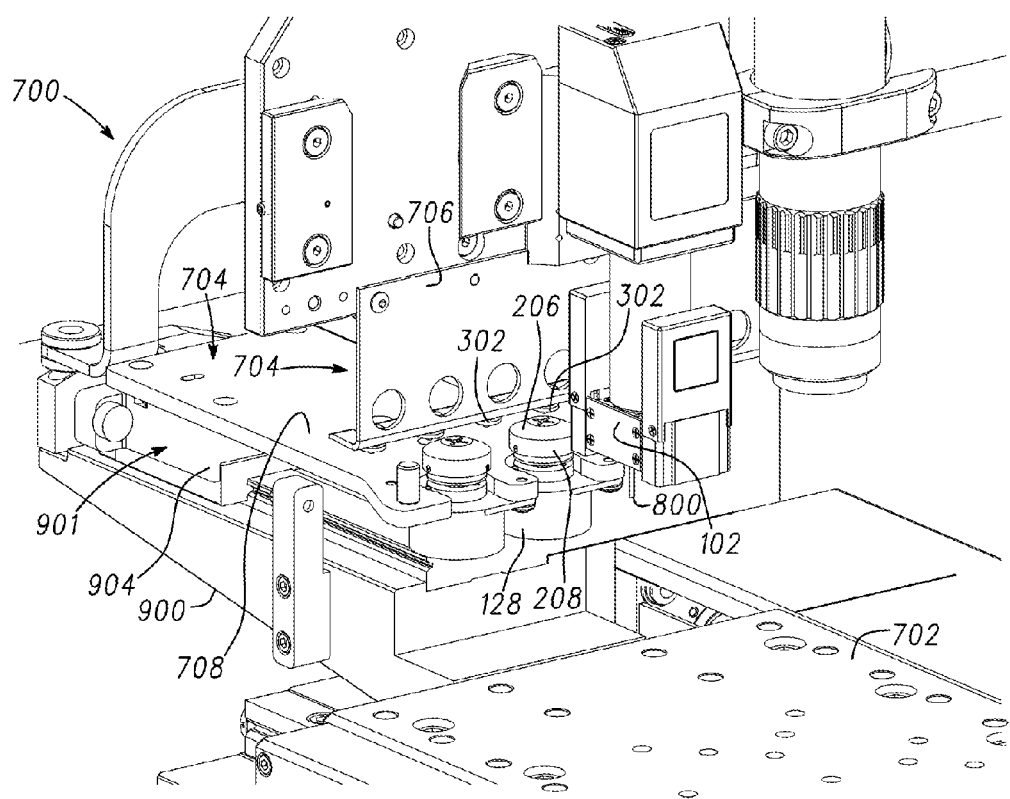
FIG. 10 is a perspective view of the deployed telescoping arm having a probe change tool aligned with a probe assembly at a probe assembly station of a probe magazine.
Figure 11:
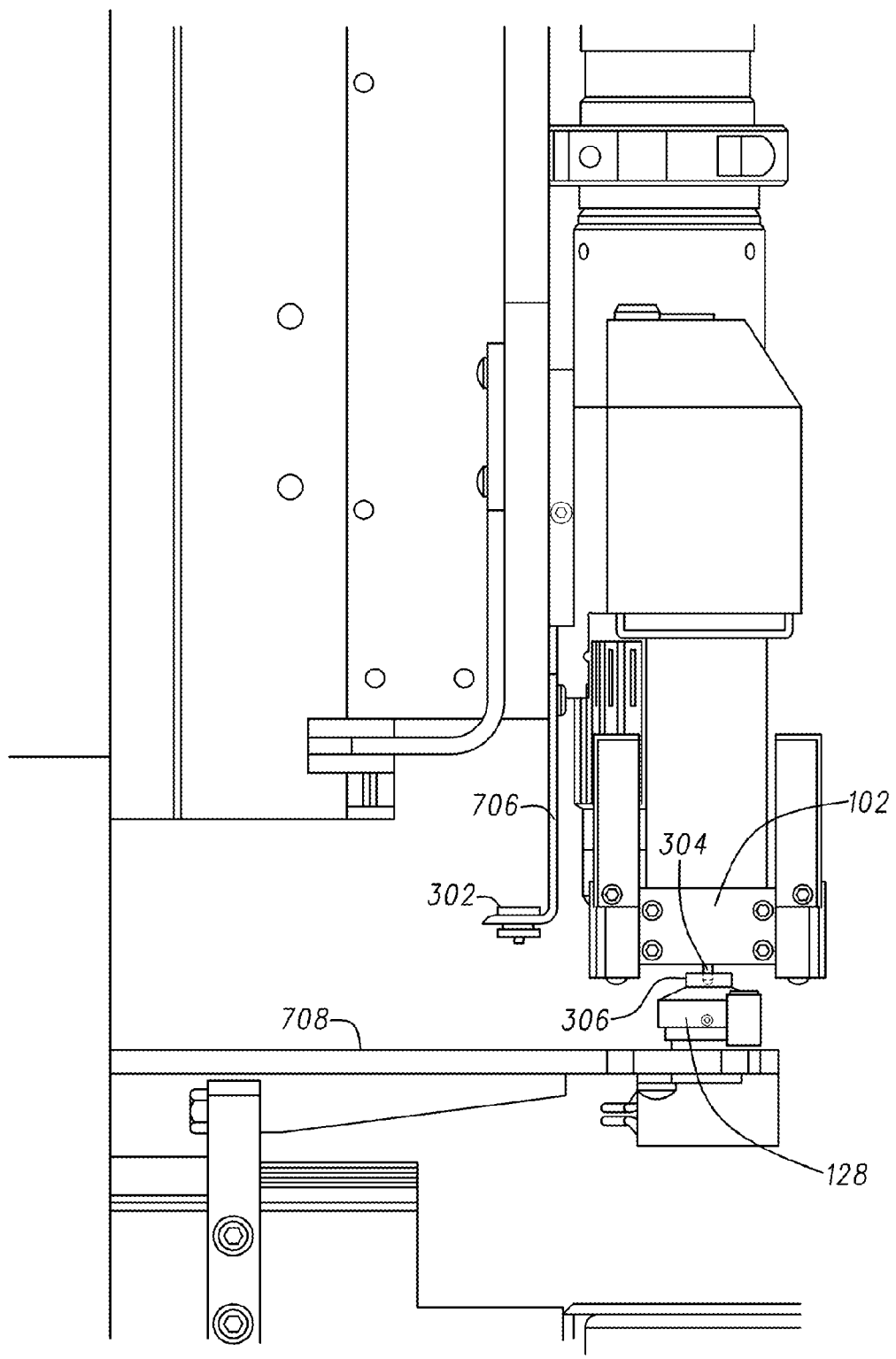
FIG. 11 is a side view of the deployed telescoping arm having the probe change tool and the probe assembly aligned with a transducer.

FIGS. 10 and 11 show the probe changing assembly 704 (e.g., the telescoping arm 708) in the deployed configuration relative to the remainder of the instrument assembly 700. As shown in FIG. 10, one of the probe changing tools 128 is aligned with the probe assembly 302 stored along the probe magazine 706. In this configuration the probe changing tool 128 is ready for elevation (or correspondingly the probe magazine 706 is ready for lowering) to thereby couple the probe assembly 302 with the receptacle socket 206 of the drive cap 208. An existing probe such as the probe 800 is shown coupled with the testing instrument 128. As further shown in FIG. 10 the probe change tools 128 are positioned in the deployed position over top of the sample stage surface 702. As described herein, coextensive positioning of the telescoping arm 708 and the probe change tools 128 relative to the sample stage surface 702 minimizes the overall footprint of the probe changing assembly 704 and the sample stage assembly 110 and thereby minimizes the overall footprint of the instrument assembly 700.

In one example the alignment of the probe change tool 128 relative to the probe magazine 706 and specifically the probe assembly 302 shown in FIG. 10 is accomplished with one or more actuators including for instance the stage actuators 114 (see FIG. 7) associated with the sample stage surface 702. As previously shown and described in FIG. 9A the arm assembly 901 is in one example coupled by way of a stage interface 902 with a sample stage surface 702 to thereby utilize the stage actuators 114 to align the probe change tool 128 with the probe assembly 302 shown in FIG. 10. In another example, the telescoping arm 708 is provided with its own aligning actuators (e.g., one or more of x, y, z or rotational actuators) configured to move the probe change tool 128 into alignment with the probe magazine 706 and the probe assembly 302 therein.

Referring now to FIG. 11, after the probe assembly 302 is coupled with one of the probe change tools 128 the probe change tool 128 is moved into alignment with the testing instrument 102. Optionally, where a probe such as the probe 800 is already installed with the testing instrument 102 the other of the probe change tools 128 is provided with a probe receptacle, such as the probe receptacle 306 shown in FIG. 3, to extract the existing probe from the testing instrument 102. In one example the other probe change tool 128 is aligned with the probe 800 in a similar fashion to the alignment of the probe assembly 302 (having a replacement probe 304) previously described herein. The probe 800 is coupled with a probe retention recess, such as the probe retention recess 310 of the probe receptacle 306, to extract the probe 800 with the probe change tool 128. The probe change tool rotates the probe 800 to decouple the probe 800 from the testing instrument 102.

After removal of the existing probe 800, the other probe change tool 128, including the replacement probe 304, is moved into alignment with the testing instrument 102 (for instance with an orifice of a center plate of a transducer 400) and the probe assembly 302 is raised (or the testing instrument 102 is lowered) to move the replacement probe 304 into close proximity with the testing instrument 102. As described herein, in an example the probe change tool 128 provides a limited torque to the probe 304 during installation. For instance, the probe change tool 128 includes a torque limiting clutch 500 shown in FIG. 5B. The torque limiting clutch 500 limits the amount of torque applied to the testing instrument 102 (e.g. including a sensitive capacitor therein) and thereby ensures installation of the probe 304 without over-torquing that may damage a capacitor of the transducer 400.

After coupling of the probe 304 with the testing instrument 102 the probe change tool 128 is lowered relative to the testing instrument 102 (and the newly installed probe 304) or alternatively the testing instrument 102 is raised relative to the probe change tool 128. The probe change tools 128 (including the empty probe receptacle 306) as well as the telescoping arm 708 are retracted into the retracted position shown in FIG. 9A. In one example an arm actuator 908 is deploys and retracts the telescoping arm 708. In yet another example, a combination of the pulling lug 910 and the lug anchor 912 shown in FIG. 9A are used to move the telescoping arm 708.

After retraction of the telescoping arm 708 into the retracted position the probe changing assembly 704 of the instrument assembly 700 is out of alignment with the sample stage surface 702 and the sample stage surface 702 (including the entirety or near to the entirety of the sample stage surface) is accessible for the testing instrument 102. Accordingly, the probe changing assembly 704 and the sample stage surface 702 occupy substantially the same area depending on the function of the instrument assembly 700. That is to say, in a testing scheme the probe changing assembly 704 is retracted out of the way of the sample stage surface 702 to allow for (full) access by the testing instrument 102. Conversely, in a probe exchanging configuration the telescoping arm 708 of the probe changing assembly 704 is deployed over a portion of the sample stage surface 702 to access the probe magazine 706 and the testing instrument 102. Accordingly, the probe changing assembly 704 and the sample stage assembly 110 occupy the same limited footprint to minimize the overall footprint of the instrument assembly 700.

Figure 12:
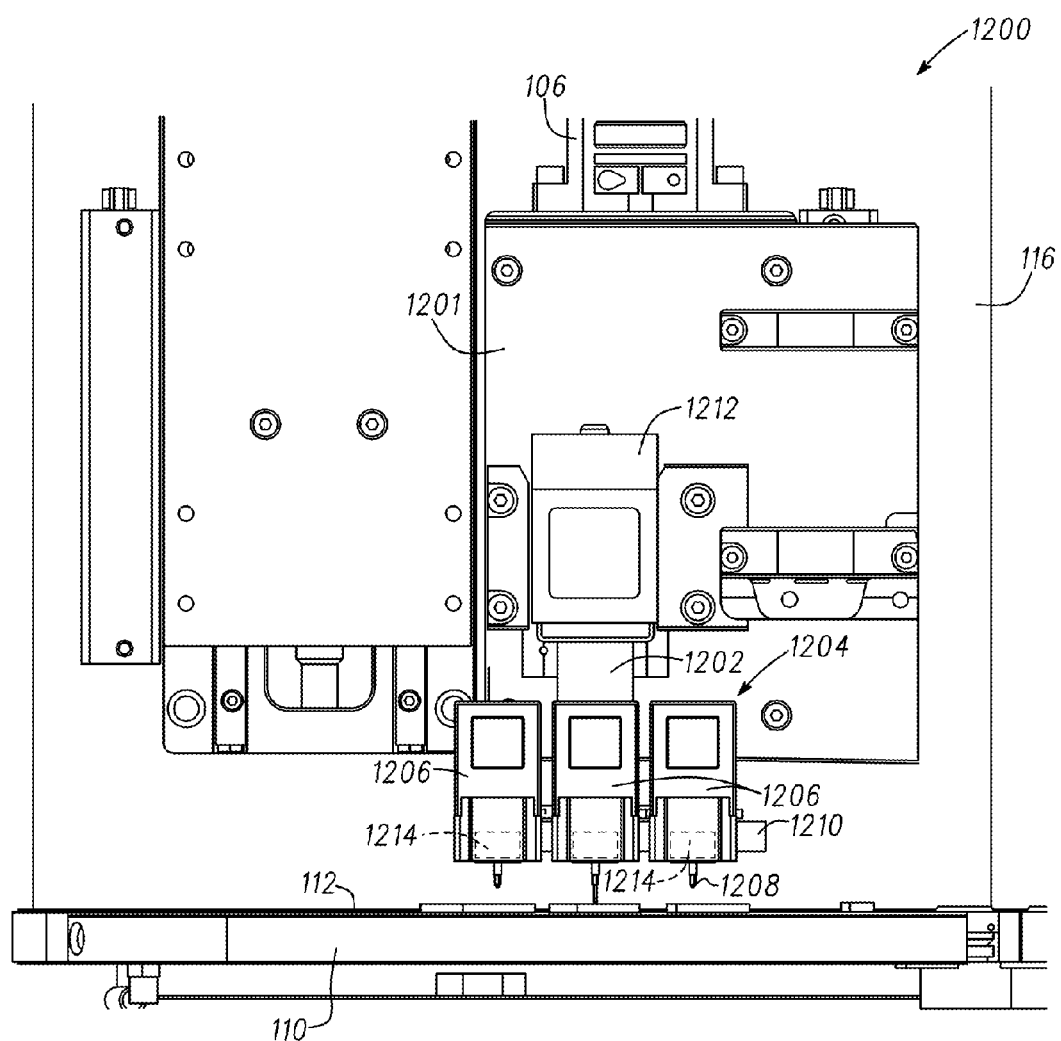
FIG. 12 is a front view of an instrument assembly including yet another example of an instrument changing assembly configured to change between a plurality of instruments each having a transducer and probe.
Figure 13:
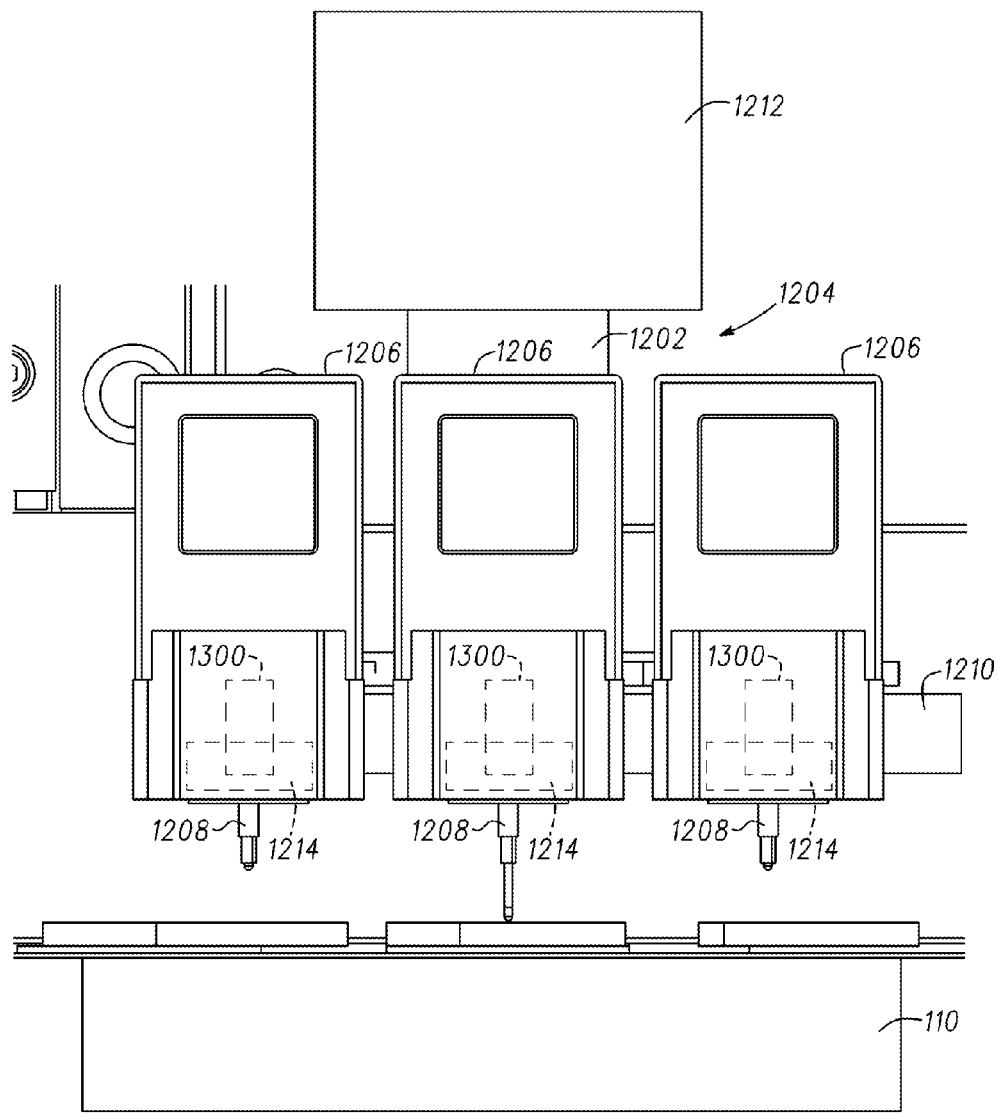
FIG. 13 is a detailed front view of the instrument changing assembly including an instrument in a deployed configuration relative to an instrument array housing.

FIGS. 12 and 13 show another example of an instrument assembly 1200. In some regards features of the instrument assembly 1200 are similar to the previously described instrument assemblies 100, 700. For instance, the instrument assembly 1200 includes a sample stage assembly 110 providing the sample stage surface 112 configured to hold a sample for testing with the instrument assembly 1200. Additionally, the instrument assembly 1200 is in one example coupled with an instrument assembly base 116 with one or more instrument mounts, an instrument actuator 106 or the like. Optionally, the instrument assembly base 116 provides the base for the sample stage assembly 110 and a plurality of stage actuators, such as the stage actuators 114 previously described and shown in FIGS. 1 and 2.

As further shown in FIG. 12, the instrument actuator 106 couples the testing instrument 1202 by way of an intervening instrument mount 1201 to the instrument assembly base 116. The testing instrument 1202 is shown in FIG. 12 and includes an instrument changing assembly 1204 configured to provide multiple component instruments 1206 for use with a testing instrument 1202. As shown in FIG. 12, the instrument changing assembly 1204 includes the plurality of component instruments 1206 positioned along an instrument array housing 1210. The instrument array housing 1210 is coupled with the overall testing instrument 1202 for instance with an optional instrument deployment actuator 1212 (or member extending from the actuator), such as a piezo actuator.

The instruments 1206, in one example, each include an instrument operating mechanism, such as a transducer 1214 and an associated probe 1208. Accordingly, each of the instruments 1206 includes a component transducer 1214 coupled with a component probe 1208. Optionally, the probes 1208 and the transducers 1214 are identical between each of the instruments 1206. In another example, one or more of the probes 1208 or the transducers 1214 vary between each of the instruments 1206 to thereby provide varying testing capabilities for the testing instrument 1202 of the instrument assembly 1200. In th example with differing component instruments 1206, the instruments 1206 are cycled (e.g., exchanged with the instrument changing assembly 1204) to provide a corresponding plurality of testing capabilities for the instrument assembly 1200. In another example, with indentical component instruments 1206, the instrument changing assembly 1204 ensures that a testing procedure is conducted continuously (including near continuously) with the instruments 1206. For instance, as one or more of the probes 1208 or transducers 1214 wears, fails to perform at threshold levels or the like that instrument 1206 is exchanged with another component instrument 1206 by the probe changing assembly 1204 (e.g., by the instrument deployment actuator 1202 described herein, the stage actuators of the stage assembly 110 or the like).

Referring again to FIG. 12, examples of the instrument deployment actuator are provided. The instrument assembly 1200 includes one or more of these exemplary instrument deployment actuators. In one example, the instrument changing assembly 1204 includes an overall instrument deployment actuator 1212 (e.g., an instrument array actuator). The instrument deployment actuator 1212 is configured to move the instruments 1206 as a unit toward or away from the sample stage surface 112. That is to say, the instrument deployment actuator 1212 provides movement to each of the instruments 1206 in a corresponding fashion to thereby position each of their probes 1208 closer or further from the sample stage surface 112.

In another example, the transducers 1214 of the component instruments 1206 provide another example of instrument deployment actuators. For instance, the instrument deployment actuator 1212 is used to position the instruments 1206 in the close proximity to the sample and the transducers 1214 are operated to accordingly deploy one or more of the probes 1208 to conduct the testing operation on the sample at a desired or identified location. That is to say, a transducer 1214 is selectively operated to move a probe 1208 of a component instrument 1206 into engagement with the sample relative to the probes 1208 of the other instruments 1206 (as well as the instrument array housing 1210).

In another example, the instrument deployment actuator includes one or more dedicated component instrument deployment actuators 1300 (shown in FIG. 13). For instance, the component instrument deployment actuators 1300 are each coupled between the instrument array housing 1210 and the respective component instrument 1206 of the plurality of instruments. In such an example, the component deployment actuators 1300 are selectively deployed relative to the other component instruments 1206 and the instrument array housing 1210.

FIG. 13 shows a detailed view of the instrument assembly 1200 previously shown in FIG. 12. As shown in FIG. 13, the instrument changing assembly 1204 includes the testing instrument 1202 having a plurality of component instruments 1206 provided along the instrument array housing 1210. In one example, the instrument array housing 1210 is coupled with an overall instrument deployment actuator such as the instrument deployment actuator 1212. The instrument deployment actuator 1212 in one example is coupled with the instrument mount 1201 (e.g., a plate as shown in FIG. 12) and the instrument mount 1201 is coupled with the instrument actuator 106. Optionally, the instrument actuator 106 provides gross control to each of the instruments 1206 (as another exemplary instrument deployment actuator) to thereby facilitate the approach of the instruments 1206 to the sample stage surface 112 while the instrument deployment actuator 1212 (associated with the testing instrument 1202) provides fine control for the approach of the plurality of instruments 1206 to the sample stage surface 112.

Each of the plurality of instruments 1206 includes a component probe 1208 as well as a corresponding transducer 1214. The transducers 1214 and the probes 1208 cooperate to perform the testing functions of each of the component instruments 1206. As shown in FIG. 13, at least two of the instruments 1206 have an identical probe 1208. In contrast, one of the instruments 1206 (the central instrument) includes another probe 1208 having a differing configuration. In one example, the probes 1208 have identical shapes, sizes and materials while in other examples the probes 1208 vary by one or more of material, size, shape or the like. Accordingly, the instruments 1206 including the corresponding transducers 1214 and the varying probes 1208 are configured to each provide one or more of identical testing capabilities or differing testing capabilities depending on the configuration of each of the instruments 1206.

Referring again to FIG. 13, a plurality of examples of instrument deployment actuators are provided. For instance, in an overall sense the instrument deployment actuator 1212 is configured to move the plurality of instruments 1206 to the sample stage surface 112. Stated another way, the instrument deployment actuator 1212 moves the instrument array housing 1210 and thereby moves each of the instruments 1206 as a unit. In another example, the instrument deployment actuators include one or more component instrument deployment actuators 1300 associated with each of the instruments 1206. As shown in FIG. 13, the component instrument deployment actuators 1300 are coupled between each of the instruments 1206 and the instrument array housing 1210 (e.g., piezo actuators or the like). The component instrument deployment actuators 1300 are configured to move each of the instruments 1206 relative to the other instruments 1206 and the instrument array housing 1210.

In one example, the actuators 106, 1212 and 1300 work in concert. After the testing instrument 1202 has approached the sample stage surface 112 with one or more of gross movement (e.g., the instrument actuator 106) and fine movement (instrument deployment actuator 1212) one or more of the instruments 1206 is deployed with the corresponding component instrument deployment actuator 1300. In yet another example, the instrument deployment actuator includes one or more of the transducers 1214 associated with each of the plurality of instruments 1206. One of the transducers 1214 is operated by way of a static voltage to present one of the probes 1208 in an extended position relative to the remainder of the probes 1208. The probe 1208 (extended relative to the other probes 1208) thereafter conducts a testing procedure in the deployed position on a sample positioned on the sample stage surface 112 (e.g., with actuation provided with a step up voltage at the transducer 1214 or with movement from the respective instrument deployment actuator 1300).

In one example, each of the instruments 1206 are indexed relative to the focal access of an optical instrument 104. As described herein, the optical instrument 104 is used in an example to identify one or more testing locations of a sample. One or more actuators (e.g., stage actuators 114 of the sample stage assembly 110) are operated to relatively move the instrument 1206 (e.g., through movement of the sample stage surface 112) between the location of the optical instrument (corresponding to the identified testing location) to thereby align the probe 1208 with the identified testing location. After the selected instrument 1206 is aligned with the identified testing location the instrument 1206 is deployed relative to the instrument array housing 1210 (e.g., relative to the remainder of the instruments 1206). In one example, a component instrument deployment actuator 1300 is used to deploy the instrument 1206. Optionally, the transducer 1214 of the instrument is used to deploy the respective probe 1208 relative to the remainder of the instrument 1206. In yet another example, transducers 1214 of the other instruments 1206 (not selected for the testing operation) are operated, for instance with a counter voltage, to withdraw the unselected probes 1208 relative to the selected probe 1208 of the selected instrument 1206.

After deployment of the instrument 1206 (for instance deployment of the probe) a testing procedure is conducted by the instrument 1206. For instance, the probe 1208 indents, scratches, pulls, compresses the sample, engages the sample for electrical characteristic testing or the like The instrument 1206 conducts the test while the remainder of the instruments 1206 are held out of contact with the sample.

In another example, where the instruments 1206 are substantially identical to one another (at least two of the instruments 1206 are identical to one another) the instrument changing assembly 1204 is operated to accordingly transition from one instrument having one or more of a worn probe 1208, a transducer 1214 providing an unsuitable mechanical response or the like to another instrument 1206 having a newer probe 1208 or transducer 1214 providing the proper mechanical response. In such an example the testing location provided by the optical instrument 104 and aligned with the previously worn instrument 1206 is used as an index location for the replacement instrument 1206. Accordingly, the sample stage assembly 110, for instance including one or more stage actuators 114, moves the identified testing location on the sample into alignment with the new (fresh) instrument 1206. The new instrument 1206 is used to test the identified testing location and thereby continues operation of the instrument assembly 1200.

By transitioning out the instruments 1206 as one or more of the components of a preceding instrument 1206 (the probe 1208 transducer 1214) wears continued operation of the instrument assembly 1200 is maintained. Accordingly, the instrument assembly 1200 including a plurality of instruments 1206 and the instrument changing assembly 1204 continues operation with little to no delay for instrument exchange. The instrument assembly 1200 remains in operation and at a later time (e.g., after working ours) one or more of the instruments 1206 having one or more of a worn probe 1208 or worn transducer 1214 is replaced. The instrument changing assembly 1204 thereby provides a magazine of instruments 1206 for use in a near continuous fashion.

VARIOUS NOTES & EXAMPLES

Example 1 can include subject matter, such as can include an instrument changing assembly comprising: a magazine having one or more probe assembly stations; at least one probe change tool including a receptacle socket; one or more probe assemblies retained within the one or more probe assembly stations of the magazine, each of the one or more probe assemblies includes: a probe receptacle including a probe retention recess and a socket fitting configured for complementary fitting with the receptacle socket, and a probe received in the probe retention recess, wherein the probe retention recess has a corresponding size and shape to the probe, and the probe retention recess has a complementary fit with the probe based on the corresponding size and shape; and wherein the socket fittings of the one or more probe assemblies have the same size and shape for complementary fitting with the receptacle socket of the at least one probe change tool, and the at least one probe change tool is configured to install or extract the respective probes from a mechanical testing instrument according to the complementary fit.

Example 2 can include, or can optionally be combined with the subject matter of Example 1, to optionally include wherein at least first and second probes of the one or more probe assemblies have one or more of different sizes or shapes from each other, and the probe retention recesses of the respective probe receptacles for the first and second probes have complementary sizes and shapes to provide the complementary fit with the respective first or second probes.

Example 3 can include, or can optionally be combined with the subject matter of one or any combination of Examples 1 or 2 to optionally include wherein the magazine includes handling prongs at each of the one or more probe assembly stations and each of the probe receptacles of the one or more probe assemblies includes a receptacle handling surface configured for handling by the handling prongs.

Example 4 can include, or can optionally be combined with the subject matter of one or any combination of Examples 1-3 to optionally include wherein the magazine includes a magazine actuator configured to move the one or more probe assemblies toward and away from the at least one probe change tool in an automated fashion.

Example 5 can include, or can optionally be combined with the subject matter of one or any combination of Examples 1-4 optionally to include wherein the socket fitting of each of the probe receptacles of the one or more probe assemblies includes one or more drive flanges, and with the socket fitting received within the receptacle socket the probe change tool is configured to rotate the probe receptacle and the probe received therein through the drive flanges.

Example 6 can include, or can optionally be combined with the subject matter of Examples 1-5 to optionally include wherein the socket fitting includes one or more magnetic drive flanges, and the one or more magnetic drive flanges guide the socket fitting into the complementary fit with the receptacle socket and retain the complementary fit with the receptacle socket.

Example 7 can include, or can optionally be combined with the subject matter of Examples 1-6 to optionally include wherein at least third and fourth probes of the one or more probe assemblies are transducer calibration weights, and the transducer calibration weights have differing weights configured to calibrate a transducer when coupled with the transducer by the at least one probe change tool.

Example 8 can include, or can optionally be combined with the subject matter of Examples 1-7 to optionally include a sample stage surface having a stage receptacle flange, and the at least one probe change tool is coupled along the stage receptacle flange.

Example 9 can include, or can optionally be combined with the subject matter of Examples 1-8 to optionally include a telescoping arm, and the at least one probe change tool is coupled near an extendable end of the telescoping arm.

Example 10 can include, or can optionally be combined with the subject matter of Examples 1-9 to optionally include wherein the telescoping arm is movable between retracted and extended positions, in the extended position the at least one probe change tool overlies a portion of a sample stage surface, and in the retracted position the at least one probe change tool is laterally spaced from the sample stage surface.

Example 11 can include, or can optionally be combined with the subject matter of Examples 1-10 to optionally include wherein the extendable end of the telescoping arm includes a pulling lug, and the pulling lug is configured for anchoring with a lug anchor coupled with an instrument.

Example 12 can include, or can optionally be combined with the subject matter of Examples 1-11 to optionally include wherein the at least one probe change tool includes a torque limiting clutch.

Example 13 can include, or can optionally be combined with the subject matter of Examples 1-12 to optionally include wherein the at least one probe change tool includes at least an installation probe change tool and an extraction probe change tool, wherein the installation probe change tool provides an installation torque, and the extraction probe change tool provides an extraction torque greater than the installation torque.

Example 14 can include, or can optionally be combined with the subject matter of Examples 1-13 to optionally include a mechanical testing instrument configured to test a sample with the probe; and a sample stage surface configured to retain the sample thereon; and the at least one probe change tool is coupled near an extendable end of a telescoping arm.

Example 15 can include, or can optionally be combined with the subject matter of Examples 1-14 to optionally include an instrument change tool and receptacle assembly comprising: a probe change tool including a rotatable tool head having a receptacle socket; a plurality of probe receptacles, each of the probe receptacles includes: a socket face including a socket fitting configured for complementary fitting with the receptacle socket, a probe face including a probe retention recess, the probe retention recess having a size and shape corresponding to a probe size and shape of a probe, and a receptacle handling surface configured for handling by a magazine having a plurality of probe assembly stations; and wherein the plurality of probe receptacles includes at least first and second probe receptacles, each of the plurality of probe receptacles include the socket fitting having the same size and shape for complementary fitting with the receptacle socket, and the probe retention recess of the first probe receptacle is configured to provide a complementary fit with a first probe size and shape, and the probe retention recess of the second probe receptacle is configured to provide a complementary fit with a second probe size and shape optionally different from the first probe size or shape.

Example 16 can include, or can optionally be combined with the subject matter of Examples 1-15 to optionally include wherein the socket fitting includes one or more drive flanges, and the probe change tool is configured to rotate a probe and the probe receptacle with the drive flanges while the probe is fit with the probe receptacle according to the complementary fit.

Example 17 can include, or can optionally be combined with the subject matter of Examples 1-16 to optionally include wherein the socket fitting includes one or more magnetic drive flanges, and the one or more magnetic drive flanges guide the socket fitting into alignment with the receptacle socket and retain the socket fitting in the complementary fit with the receptacle socket.

Example 18 can include, or can optionally be combined with the subject matter of Examples 1-17 to optionally include wherein the socket fitting is configured for complementary fitting within the receptacle socket.

Example 19 can include, or can optionally be combined with the subject matter of Examples 1-18 to optionally include first and second probes, the first probe having the first probe size and shape, and second probe having the second probe size and shape different from the first probe size or shape.

Example 20 can include, or can optionally be combined with the subject matter of Examples 1-19 to optionally include at least third and fourth probes including transducer calibration weights, and the transducer calibration weights have differing weights configured to calibrate a transducer when coupled with the transducer by the at least one probe change tool.

Example 21 can include, or can optionally be combined with the subject matter of Examples 1-20 to optionally include wherein the probe change tool includes a torque limiting clutch.

Example 22 can include, or can optionally be combined with the subject matter of Examples 1-21 to optionally include a mechanical testing instrument configured to test a sample with a probe; a sample stage surface configured to retain the sample thereon; and a magazine having two or more probe assembly stations, and each of the probe receptacles of the plurality of probe receptacles are received within respective probe assembly stations.

Example 23 can include, or can optionally be combined with the subject matter of Examples 1-22 to optionally include one or more actuators configured to move the probe change tool and a probe receptacle of the plurality of probe receptacles between a magazine storing the plurality of probe receptacles and a mechanical testing instrument configured to test a sample with a probe, the one or more actuators move the probe change tool automatically.

Example 24 can include, or can optionally be combined with the subject matter of Examples 1-23 to optionally include a method for automated changing of an instrument of a mechanical testing instrument comprising: removing a probe assembly from a magazine, the probe assembly includes a probe receptacle including a probe retention recess and a socket fitting, the probe retention recess having a complementary fit to a probe within the probe retention recess, removing including: aligning a probe change tool with the probe assembly in the magazine with one or more actuators, and coupling a receptacle socket of the probe change tool with the socket fitting of the probe assembly, the receptacle socket having a complementary fit to the socket fitting, installing the probe to a mechanical testing instrument including: aligning the probe change tool having the probe assembly with the mechanical testing instrument with the one or more actuators, and rotating the probe assembly with the probe change tool, rotation of the probe change tool rotating the probe into an installed configuration with the mechanical testing instrument by rotation of the probe receptacle; and withdrawing the probe change tool and the probe receptacle from the installed probe and the mechanical testing instrument with the one or more actuators.

Example 25 can include, or can optionally be combined with the subject matter of Examples 1-24 to optionally include wherein removing the probe assembly from the magazine includes: lowering the magazine to the probe change tool, and fitting the socket fitting into the receptacle socket according to the lowering.

Example 26 can include, or can optionally be combined with the subject matter of Examples 1-25 to optionally include wherein fitting the socket fitting includes fitting drive flanges of the socket fitting into the receptacle socket.

Example 27 can include, or can optionally be combined with the subject matter of Examples 1-26 to optionally include wherein fitting the socket fitting includes: guiding the socket fitting into the complementary fit with the receptacle socket with magnetic drive flanges, and retaining the complementary fit with the magnetic drive flanges.

Example 28 can include, or can optionally be combined with the subject matter of Examples 1-27 to optionally include wherein one or more of aligning the probe change tool with the probe assembly or aligning the probe change tool with the probe assembly with the mechanical testing instrument includes moving a sample stage surface, and the probe change tool is coupled along a stage receptacle flange of the sample stage surface.

Example 29 can include, or can optionally be combined with the subject matter of Examples 1-28 to optionally include wherein one or more of aligning the probe change tool with the probe assembly or aligning the probe change tool with the probe assembly with the mechanical testing instrument includes moving the probe change tool over a sample stage surface with a telescoping arm.

Example 30 can include, or can optionally be combined with the subject matter of Examples 1-29 to optionally include wherein one or more of aligning the probe change tool includes anchoring a pulling lug with a lug anchor of the mechanical testing instrument, and moving the mechanical testing instrument to move the probe change tool over the sample stage surface.

Example 31 can include, or can optionally be combined with the subject matter of Examples 1-30 to optionally include reading probe calibration information from a probe or probe indicia, associating the probe calibration information with at least one probe assembly station of the magazine, and automatically calibrating a transducer of the mechanical testing instrument with the probe calibration information with one or more of removal of the probe assembly including the probe from the associated probe assembly station or installing the probe.

Example 32 can include, or can optionally be combined with the subject matter of Examples 1-31 to optionally include wherein installing the probe includes rotating the probe assembly with the probe change tool including a torque limiting clutch.

Example 33 can include, or can optionally be combined with the subject matter of Examples 1-32 to optionally include extracting an existing probe from the mechanical testing instrument with the probe change tool.

Example 34 can include, or can optionally be combined with the subject matter of Examples 1-33 to optionally include wherein the probe change tool includes an installation probe change tool and an extraction probe change tool, installing the probe includes rotating the probe assembly with the installation probe change tool at an installation torque, and extracting the existing probe from the mechanical testing instrument includes rotating the probe assembly with the extraction probe change tool at an extraction torque greater than the installation torque.

Example 35 can include, or can optionally be combined with the subject matter of Examples 1-34 to optionally include calibration of the mechanical testing instrument including: installing a first calibration probe having a first calibration weight to a transducer of the mechanical testing instrument with the probe change tool; conducting a transducer calibration to measure a transducer response with the first calibration weight; placing the first calibration probe within a magazine with the probe change tool; installing a second calibration probe having a second calibration weight to the transducer with the probe change tool, the second calibration weight having a different weight relative to the first calibration weight; conducting the transducer calibration to measure the transducer response with the second calibration weight; comparing the transducer response with the first and second calibration weights to predicted transducer calibration responses; and calibrating the transducer according to the comparison.

Example 36 can include, or can optionally be combined with the subject matter of Examples 1-35 to optionally include wherein installing the first calibration probe to the transducer of the mechanical testing instrument with the probe change tool includes installing the first calibration probe coupled with a second probe receptacle, the second probe receptacle having a socket fitting providing a complementary fit with the receptacle socket of the probe change tool, and installing the second calibration probe to the transducer of the mechanical testing instrument with the probe change tool includes coupled the second calibration probe coupled with a third probe receptacle, the second probe receptacle having a socket fitting providing a complementary fit with the receptacle socket of the probe change tool.

Example 37 can include, or can optionally be combined with the subject matter of Examples 1-36 to optionally include an instrument changing assembly comprising: an instrument array housing; a plurality of instruments coupled along the instrument array housing at instrument stations, each of the instruments of the plurality of instruments including a probe; and an instrument deployment actuator associated with one or more instruments of the plurality of instruments, the instrument deployment actuator configured to deploy at least one of the instruments relative to the instrument array housing.

Example 38 can include, or can optionally be combined with the subject matter of Examples 1-37 to optionally include wherein the instrument deployment actuator includes an instrument array actuator coupled with the instrument array housing.

Example 39 can include, or can optionally be combined with the subject matter of Examples 1-38 to optionally include wherein the instrument array actuator includes a z-axis actuator configured to move each of the plurality of instruments together toward a sample.

Example 40 can include, or can optionally be combined with the subject matter of Examples 1-39 to optionally include wherein each of the instruments of the plurality of instruments includes a respective transducer coupled with each probe of each instrument, and the transducer of each instrument deploys and the respective probe are deployed relative to the probes of the other instruments of the plurality of instruments.

Example 41 can include, or can optionally be combined with the subject matter of Examples 1-40 to optionally include wherein each of the instruments of the plurality of instruments includes a respective transducer coupled with each probe of each of the instruments.

Example 42 can include, or can optionally be combined with the subject matter of Examples 1-41 to optionally include wherein the instrument deployment actuator includes a plurality of transducers of the plurality of instruments, each of the transducers is configured to deploy the respective probe relative to the other probes of the plurality of instruments.

Example 43 can include, or can optionally be combined with the subject matter of Examples 1-42 to optionally include wherein the instrument deployment actuator includes a plurality of instrument deployment actuators coupled along the instrument array housing at the instrument stations, each instrument deployment actuator associated with a respective instrument of the plurality of instruments and configured to deploy the respective instrument relative to the other instruments of the plurality of instruments.

Example 44 can include, or can optionally be combined with the subject matter of Examples 1-43 to optionally include wherein the plurality of instruments includes at least a first instrument and a second instrument, and the first and second instruments are different.

Example 45 can include, or can optionally be combined with the subject matter of Examples 1-44 to optionally include wherein the first instrument includes a first transducer configured to provide a first range of forces to a first probe coupled with the first transducer, and the second instrument includes a second different transducer configured to provide a second range of forces to a second probe coupled with the second probe, the first and second range of forces are different.

Example 46 can include, or can optionally be combined with the subject matter of Examples 1-45 to optionally include wherein the first instrument includes a first probe having at least first probe characteristic, and the second instrument includes a second probe having a second probe characteristics different from the first probe characteristic.

Each of these non-limiting examples can stand on its own, or can be combined in any permutation or combination with any one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An instrument changing assembly comprising:
a magazine having one or more probe assembly stations;
at least one probe change tool including a receptacle socket;
one or more probe assemblies retained within the one or more probe assembly stations of the magazine, each of the one or more probe assemblies includes:
a probe receptacle including a probe retention recess and a socket fitting configured for complementary fitting with the receptacle socket, and
a probe received in the probe retention recess, wherein the probe retention recess has a corresponding size and shape to the probe, and the probe retention recess has a complementary fit with the probe based on the corresponding size and shape; and
wherein the socket fittings of the one or more probe assemblies have the same size and shape for complementary fitting with the receptacle socket of the at least one probe change tool, and the at least one probe change tool is configured to install or extract the respective probes from a mechanical testing instrument according to the complementary fit.

2. The instrument changing assembly of claim 1, wherein at least first and second probes of the one or more probe assemblies have one or more of different sizes or shapes from each other, and
the probe retention recesses of the respective probe receptacles for the first and second probes have complementary sizes and shapes to provide the complementary fit with the respective first or second probes.

3. The instrument changing assembly of claim 1, wherein the magazine includes handling prongs at each of the one or more probe assembly stations and each of the probe receptacles of the one or more probe assemblies includes a receptacle handling surface configured for handling by the handling prongs.

4. The instrument changing assembly of claim 1, wherein the magazine includes a magazine actuator configured to move the one or more probe assemblies toward and away from the at leak one probe change tool in an automated fashion.

5. The instrument changing assembly of claim 1, wherein the socket fitting of each of the probe receptacles of the one or more probe assemblies includes one or more drive flanges, and with the socket fitting received within the receptacle socket the probe change tool is configured to rotate the probe receptacle and the probe received therein through the drive flanges.

6. The instrument changing assembly of claim 1, wherein the socket fitting includes one or more magnetic drive flanges, and the one or more magnetic drive flanges guide the socket fitting into the complementary fit with the receptacle socket and retain the complementary fit with the receptacle socket.

7. The instrument changing assembly of claim 1, wherein at least third and fourth probes of the one or more probe assemblies are transducer calibration weights, and the transducer calibration weights have differing weights configured to calibrate a transducer when coupled with the transducer by the at least one probe change tool.

8. The instrument changing assembly of claim 1 comprising a sample stage surface having a stage receptacle flange, and the at least one probe change tool is coupled along the stage receptacle flange.

9. The instrument changing assembly of claim 1 comprising a telescoping arm, and the at least one probe change tool is coupled near an extendable end of the telescoping arm.

10. The instrument changing assembly of claim 9, wherein the telescoping arm is movable between retracted and extended positions,
in the extended position the at least one probe change tool overlies a portion of a sample stage surface, and
in the retracted position the at least one probe change tool is laterally spaced from the sample stage surface.

11. The instrument changing assembly of claim 1, wherein the at least one probe change tool includes a torque limiting clutch.

12. The instrument changing assembly of claim 1, wherein the at least one probe change tool includes at least an installation probe change tool and an extraction probe change tool, wherein the installation probe change tool provides an installation torque, and the extraction probe change tool provides an extraction torque greater than the installation torque.

13. The instrument changing assembly of claim 1 comprising:
a mechanical testing instrument configured to test a sample with the probe; and
a sample stage surface configured to retain the sample thereon; and
the at least one probe change tool is coupled near an extendable end of a telescoping arm.

14. An instrument change tool and receptacle assembly comprising:
a probe change tool including a rotatable tool head having a receptacle socket;
a plurality of probe receptacles, each of the probe receptacles includes:
a socket face including a socket fitting configured for complementary fitting with the receptacle socket,
a probe face including a probe retention recess, the probe retention recess having a size and shape corresponding to a probe size and shape of a probe, and
a receptacle handling surface configured for handling by a magazine having a plurality of probe assembly stations; and
wherein the plurality of probe receptacles includes at least first and second probe receptacles, each of the plurality of probe receptacles include the socket fitting having the same size and shape for complementary fitting with the receptacle socket, and
the probe retention recess of the first probe receptacle is configured to provide a complementary fit with a first probe size and shape, and
the probe retention recess of the second probe receptacle is configured to provide a complementary fit with a second probe size and shape.

15. The instrument changing assembly of claim 14, wherein the socket fitting includes one or more drive flanges, and the probe change tool is configured to rotate a probe and the probe receptacle with the drive flanges while the probe is fit with the probe receptacle according to the complementary fit.

16. The instrument changing assembly of claim 14, wherein the socket fitting includes one or more magnetic drive flanges, and the one or more magnetic drive flanges guide the socket fitting into alignment with the receptacle socket and retain the socket fitting in the complementary fit with the receptacle socket.

17. The instrument changing assembly of claim 14 comprising first and second probes, the first probe having the first probe size and shape, and second probe having the second probe size and shape different from the first probe size or shape.

18. The instrument changing assembly of claim 14 comprising at least third and fourth probes including transducer calibration weights, and the transducer calibration weights have differing weights configured to calibrate a transducer when coupled with the transducer by the at least one probe change tool.

19. The instrument changing assembly of claim 14, wherein the probe change tool includes a torque limiting clutch.

20. The instrument changing assembly of claim 14 comprising:
a mechanical testing instrument configured to test a sample with a probe;
a sample stage surface configured to retain the sample thereon; and
a magazine having two or more probe assembly stations, and each of the probe receptacles of the plurality of probe receptacles are received within respective probe assembly stations.

21. The instrument changing assembly of claim 14 comprising one or more actuators configured to move the probe change tool and a probe receptacle of the plurality of probe receptacles between a magazine storing the plurality of probe receptacles and a mechanical testing instrument configured to test a sample with a probe, the one or more actuators move the probe change tool automatically.

22. A method for automated changing of an instrument of a mechanical testing instrument comprising:
removing a probe assembly from a magazine, the probe assembly includes a probe receptacle including a probe retention recess and a socket fitting, the probe retention recess having a complementary fit to a probe within the probe retention recess, removing including:
aligning a probe change tool with the probe assembly in the magazine with one or more actuators, and
coupling a receptacle socket of the probe change tool with the socket fitting of the probe assembly, the receptacle socket having a complementary fit to the socket fitting, installing the probe to a mechanical testing instrument including:
aligning the probe change tool having the probe assembly with the mechanical testing instrument with the one or more actuators, and
rotating the probe assembly with the probe change tool, rotation of the probe change tool rotating the probe into an installed configuration with the mechanical testing instrument by rotation of the probe receptacle; and withdrawing the probe change tool and the probe receptacle from the installed probe and the mechanical testing instrument with the one or more actuators.

23. The method of claim 22, wherein removing the probe assembly from the magazine includes:
lowering the magazine to the probe change tool, and
fitting the socket fitting into the receptacle socket according to the lowering.

24. The method of claim 23, wherein fitting the socket fitting includes fitting drive flanges of the socket fitting into the receptacle socket.

25. The method of claim 23, wherein fitting the socket fitting includes:
guiding the socket fitting into the complementary fit with the receptacle socket with magnetic drive flanges, and
retaining the complementary fit with the magnetic drive flanges.

26. The method of claim 22, wherein one or more of aligning the probe change tool with the probe assembly or aligning the probe change tool with the probe assembly with the mechanical testing instrument includes moving a sample stage surface; and the probe change tool is coupled along a stage receptacle flange of the sample stage surface.

27. The method of claim 22, wherein one or more of aligning the probe change tool with the probe assembly or aligning the probe change tool with the probe assembly with the mechanical testing instrument includes moving the probe change tool over a sample stage surface with a telescoping arm.

28. The method of claim 22 comprising:
reading probe calibration information from a probe or probe indicia,
associating the probe calibration information with at least one probe assembly station of the magazine, and
automatically calibrating a transducer of the mechanical testing instrument with the probe calibration information with one or more of removal of the probe assembly including the probe from the associated probe assembly station or installing the probe.

29. The method of claim 28, wherein the probe change tool includes an installation probe change tool and an extraction probe change tool,
installing the probe includes rotating the probe assembly with the installation probe change tool at an installation torque, and
extracting the existing probe from the mechanical testing instrument includes rotating the probe assembly with the extraction probe change tool at an extraction torque greater than the installation torque.

30. The method of claim 22 comprising extracting an existing probe from the mechanical testing instrument with the probe change tool.

31. The method of claim 22 comprising calibration of the mechanical testing instrument including:
installing a first calibration probe having a first calibration weight to a transducer of the mechanical testing instrument with the probe change tool;
conducting a transducer calibration to measure a transducer response with the first calibration weight;
placing the first calibration probe within a magazine with the probe change tool;
installing a second calibration probe having a second calibration weight to the transducer with the probe change tool, the second calibration weight having a different weight relative to the first calibration weight;
conducting the transducer calibration to measure the transducer response with the second calibration weight;
comparing the transducer response with the first and second calibration weights to predicted transducer calibration responses; and
calibrating the transducer according to the comparison.

32. The method of claim 31, wherein installing the first calibration probe to the transducer of the mechanical testing instrument with the probe change tool includes installing the first calibration probe coupled with a second probe receptacle, the second probe receptacle having a socket fitting providing a complementary fit with the receptacle socket of the probe change tool, and
installing the second calibration probe to the transducer of the mechanical testing instrument with the probe change tool includes coupled the second calibration probe coupled with a third probe receptacle, the second probe receptacle having a socket fitting providing a complementary fit with the receptacle socket of the probe change tool.

* * * * *

UNITED STATES PATENT AND TRADEMARK OFFICE
CERTIFICATE OF CORRECTION

PATENT NO. : 9,902,027 B2  
APPLICATION NO. : 14/908809  
DATED : February 27, 2018  
INVENTOR(S) : Dama et al.

Page 1 of 1

It is certified that error appears in the above-identified patent and that said Letters Patent is hereby corrected as shown below:

In the Claims

In Column 34, Line 57, in Claim 4, delete "leak" and insert --least-- therefor

In Column 37, Line 23, in Claim 26, delete "surface;" and insert --surface,-- therefor Signed and Sealed this  
Twenty-eighth Day of May, 2019

Andrei Iancu  
*Director of the United States Patent and Trademark Office*